(12) United States Patent
DeCarolis et al.

(10) Patent No.: US 7,829,311 B2
(45) Date of Patent: *Nov. 9, 2010

(54) KETOSTEROID ISOMERASE INCLUSION BODY TAG ENGINEERED TO BE ACID-RESISTANT BY REPLACING ASPARTATES WITH GLUTAMATE

(75) Inventors: Linda Jane DeCarolis, Wilmington, DE (US); Stephen R. Fahnestock, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 116 days.

This patent is subject to a terminal disclaimer.

(21) Appl. No.: 12/172,385

(22) Filed: Jul. 14, 2008

(65) Prior Publication Data

US 2009/0029420 A1    Jan. 29, 2009

Related U.S. Application Data

(60) Provisional application No. 60/951,993, filed on Jul. 26, 2007, provisional application No. 60/951,754, filed on Jul. 25, 2007.

(51) Int. Cl.
- *C12P 21/04* (2006.01)
- *C12N 9/90* (2006.01)
- *C12N 15/00* (2006.01)
- *C12N 1/20* (2006.01)
- *C07K 14/00* (2006.01)

(52) U.S. Cl. .................. 435/69.7; 435/233; 435/320.1; 435/252.3; 435/252.33; 530/350

(58) Field of Classification Search .................. None
See application file for complete search history.

(56) References Cited

U.S. PATENT DOCUMENTS

| | | |
|---|---|---|
| 5,206,154 A | 4/1993 | Lai et al. |
| 5,215,896 A | 6/1993 | Keck et al. |
| 5,223,409 A | 6/1993 | Ladner et al. |
| 5,302,526 A | 4/1994 | Keck et al. |
| 5,330,902 A | 7/1994 | Keck et al. |
| 5,403,484 A | 4/1995 | Ladner et al. |
| 5,449,754 A | 9/1995 | Nishioka |
| 5,480,971 A | 1/1996 | Houghten et al. |
| 5,571,698 A | 11/1996 | Ladner et al. |
| 5,585,275 A | 12/1996 | Hudson et al. |
| 5,639,603 A | 6/1997 | Dower et al. |
| 5,643,768 A | 7/1997 | Kawasaki |
| 5,648,244 A | 7/1997 | Kuliopulos et al. |
| 5,658,754 A | 8/1997 | Kawasaki |
| 5,837,500 A | 11/1998 | Ladner et al. |
| 6,037,145 A | 3/2000 | Yabuta et al. |
| 6,207,446 B1 | 3/2001 | Szostak et al. |
| 6,214,553 B1 | 4/2001 | Szostak et al. |
| 6,242,219 B1 | 6/2001 | Better et al. |
| 6,258,558 B1 | 7/2001 | Szostak et al. |
| 6,261,804 B1 | 7/2001 | Szostak et al. |
| 6,281,344 B1 | 8/2001 | Szostak et al. |
| 6,312,927 B1 | 11/2001 | Hammond |
| 6,416,950 B1 | 7/2002 | Lohse et al. |
| 6,429,300 B1 | 8/2002 | Kurz et al. |
| 6,436,665 B1 | 8/2002 | Kuimelis |
| 6,518,018 B1 | 2/2003 | Szostak et al. |
| 6,602,685 B1 | 8/2003 | Lohse |
| 6,613,548 B1 | 9/2003 | Chu |
| 6,620,419 B1 | 9/2003 | Lintner |
| 6,696,089 B2 | 2/2004 | Kabanov et al. |
| 6,815,426 B2 | 11/2004 | Scialdone et al. |
| 6,846,655 B1 | 1/2005 | Wagner et al. |
| 7,074,557 B2 | 7/2006 | Osbourn et al. |
| 7,078,197 B2 | 7/2006 | Kurz et al. |
| 7,220,405 B2 | 5/2007 | Huang et al. |
| 7,276,088 B2 | 10/2007 | Huang et al. |
| 7,285,264 B2 | 10/2007 | O'Brien et al. |
| 7,309,482 B2 | 12/2007 | Buseman-Williams et al. |
| 7,427,656 B2 | 9/2008 | Decarolis et al. |
| 7,678,883 B2 * | 3/2010 | Cheng et al. ................. 530/324 |
| 2002/0098524 A1 | 7/2002 | Murray et al. |
| 2003/0152976 A1 | 8/2003 | Janssen et al. |
| 2003/0185870 A1 | 10/2003 | Grinstaff et al. |

(Continued)

FOREIGN PATENT DOCUMENTS

WO    WO9404688    3/1994

(Continued)

OTHER PUBLICATIONS

Rodriguez et al., Prot. Expression Purif. 28:224-231, 2003.*

(Continued)

*Primary Examiner*—David J Steadman

(57) ABSTRACT

An acid-resistant peptide solubility tag (an "inclusion body tag") is provided that is effective in producing peptides of interest in an insoluble form. Fusion peptide constructs comprising the inclusion body tag fused to a peptide of interest are provided. An acid cleavable peptide moiety separates the inclusion body tag from the peptide of interest so that acid hydrolysis can be used during subsequent processing steps to separate the tag from the desired peptide of interest. The present inclusion body tag's resistance to acid hydrolysis facilitates easier and cleaner separation of the peptide of interest after acid hydrolysis. Specifically, a ketosteroid isomerase-derived inclusion body tag is provided that has been engineered to be more resistant to acid hydrolysis.

15 Claims, 3 Drawing Sheets

U.S. PATENT DOCUMENTS

| | | |
|---|---|---|
| 2005/0221444 A1 | 10/2005 | Williams et al. |
| 2007/0065387 A1 | 3/2007 | Beck et al. |
| 2008/0107614 A1 | 5/2008 | Fahnestock et al. |
| 2008/0175798 A1 | 7/2008 | Beck et al. |

FOREIGN PATENT DOCUMENTS

| | | |
|---|---|---|
| WO | WO0179479 | 10/2001 |
| WO | WO2004000257 | 12/2003 |
| WO | WO2004048399 | 6/2004 |

OTHER PUBLICATIONS

Kemp, D. J., Proc. Natl. Acad. Sci. USA 78(7): 4520-4524 (1981).
Chien et al., Proc. Natl. Acad. Sci. USA 88(21): 9578-82 (1991).
Deshpande, Mukund V., Appl. Biochem. Biotechnol., 36:227 (1992).
Dykes et al., Eur. J. Biochem., 174:411 (1988).
Schellenberger et al., Int. J. Peptide Protein Res., 41:326 (1993).
Shen et al., Proc. Nat. Acad. Sci. USA 81:4627 (1984).
Kempe et al., Gene, 39:239 (1985).
Ray et al., Bio/Technology, 11:64 (1993).
Lai et al., Antimicrob. Agents & Chemo., 37:1614 (1993).
Gram et al., Bio/Technology, 12:1017 (1994).
Kuliopulos et al., J. Am. Chem. Soc. 116:4599-4607 (1994).
Pilon et al., Biotechnol. Prog., 13:374-79 (1997).
Haught et al., Biotechnol. Bioengineer. 57:55-61 (1998).
Sulter et al., Arch. Microbiol., 153:485-489 (1990).
Tyas et al., EMBO Reports, 1(3):266-270 (2000).
Thornberry et al., J. Biol. Chem., 272:17907-17911 (1997).
Szoka et al., DNA, 5(1):11-20 (1986).
Bellion et al., Microb. Growth C1 Compd., [Int. Symp.], 7th (1993), 415-32.
Gavit, P. and Better, M., J. Biotechnol., 79:127-136 (2000).
The Following Applications Are Commonly Owned by Dupont and Are Reported Herein: U.S. Appl. No. 11/607,672, filed Dec. 1, 2006; U.S. Appl. No. 11/607,673, filed Dec. 1, 2006; U.S. Appl. No. 11/607,792, filed Dec. 1, 2006; U.S. Appl. No. 10/935,254, filed Sep. 7, 2004; U.S. Appl. No. 11/512,910, filed Aug. 30, 2006; U. S. Appl. No. 11/696,380, filed Apr. 4, 2007.
The Following Applications Are Commonly Owned by Dupont and Are Reported Herein: U.S. Appl. No. 11/877,692, filed Oct. 24, 2007; U.S. Appl. No. 11/607,723, filed Dec. 1, 2006; U.S. Appl. No. 11/607,734, filed Dec. 1, 2006; U.S. Appl. No. 60/951,754, filed Jul. 25, 2007.

* cited by examiner

CLUSTAL W (1.83) multiple sequence alignment

```
KSI-C4   MHTPEHITAVVQRFVAALNAGDLDGIVALFADDDATVEEPVGSEPRSGTAACREFYANSLK
KSI-C4E  MHTPEHITAVVQRFVAALNAGELEGIVALFAEEATVEEPVGSEPRSGTAACREFYANSLK
         *****************   :*:**** ::*************************

KSI-C4   LPLAVELTQECRAVANEAAFAFTVSFEYQGRKTVVAPCDHFRFNGAGKVVSIRALFGEKN
KSI-C4E  LPLAVELTQECRAVANEAAFAFTVSFEYQGRKTVVAPCEHFRFNGAGKVVSIRALFGEKN
         **************************************:*********************

KSI-C4   IHACQGSD        (SEQ ID NO: 4)
KSI-C4E  IHACQGSD        (SEQ ID NO: 2)
         ********
```

FIG. 1

KETOSTEROID ISOMERASE INCLUSION BODY TAG ENGINEERED TO BE ACID-RESISTANT BY REPLACING ASPARTATES WITH GLUTAMATE

This application claims the benefit of U.S. Provisional Application No. 60/951,993 filed Jul. 26, 2007 and U.S. Provisional Application No. 60/951,754 filed Jul. 25, 2007; each of which in its entirety is incorporated herein by reference.

FIELD OF THE INVENTION

The invention relates to the field of protein expression and purification from microbial cells. More specifically, an acid-resistant peptide tag is provided useful in the generation of insoluble fusion proteins.

BACKGROUND OF THE INVENTION

The efficient production of bioactive proteins and peptides has become a hallmark of the biomedical and industrial biochemical industry. Bioactive peptides and proteins are used as curative agents in a variety of diseases such as diabetes (insulin), viral infections and leukemia (interferon), diseases of the immune system (interleukins), and red blood cell deficiencies (erythropoietin) to name a few. Additionally, large quantities of proteins and peptides are needed for various industrial applications including, for example, the pulp and paper and pulp industries, textiles, food industries, personal care and cosmetics industries, sugar refining, wastewater treatment, production of alcoholic beverages and as catalysts for the generation of new pharmaceuticals.

With the advent of the discovery and implementation of combinatorial peptide screening technologies such as bacterial display (Kemp, D. J.; Proc. Natl. Acad. Sci. USA 78(7): 4520-4524 (1981); yeast display (Chien et al., Proc. Nat. Acad. Sci. USA 88(21): 9578-82 (1991)), combinatorial solid phase peptide synthesis (U.S. Pat. Nos. 5,449,754; 5,480,971; 5,585,275 and 5,639,603), phage display technology (U.S. Pat. Nos. 5,223,409; 5,403,484; 5,571,698; and 5,837,500), ribosome display (U.S. Pat. Nos. 5,643,768; 5,658,754; and 7,074,557), and mRNA display technology (PROFUSION™; U.S. Pat. Nos. 6,258,558; 6,518,018; 6,281,344; 6,214,553; 6,261,804; 6,207,446; 6,846,655; 6,312,927; 6,602,685; 6,416,950; 6,429,300; 7,078,197; and 6,436,665) new applications for peptides having binding affinities have been developed. In particular, peptides are being looked to as linkers in biomedical fields for the attachment of diagnostic and pharmaceutical agents to surfaces (see Grinstaff et al, U.S. Patent Application Publication No. 2003/0185870 and Lintner in U.S. Pat. No. 6,620,419), as well as in the personal care industry for the attachment of benefit agents to body surfaces such as hair and skin (see commonly owned U.S. Pat. No. 7,220,405, and U.S. Patent Application Publication No. 2003/0152976 to Janssen et al.), and in the printing industry for the attachment of pigments to print media (see commonly owned U.S. patent Application Publication No. 2005/0054752).

In some cases commercially useful proteins and peptides may be synthetically generated or isolated from natural sources. However, these methods are often expensive, time consuming and characterized by limited production capacity. The preferred method of protein and peptide production is through the fermentation of recombinantly constructed organisms, engineered to over-express the protein or peptide of interest. Although preferable to synthesis or isolation, recombinant expression of peptides has a number of obstacles to be overcome in order to be a cost-effective means of production. For example, peptides (and in particular short peptides) produced in a cellular environment are susceptible to degradation from the action of native cellular proteases. Additionally, purification can be difficult, resulting in poor yields depending on the nature of the protein or peptide of interest.

One means to mitigate the above difficulties is the use the genetic chimera for protein and peptide expression. A chimeric protein or "fusion protein" is a polypeptide comprising at least one portion of the desired protein product fused to at least one portion comprising a peptide tag. The peptide tag may be used to assist protein folding, assist post expression purification, protect the protein from the action of degradative enzymes, and/or assist the protein in passing through the cell membrane.

In many cases it is useful to express a protein or peptide in insoluble form, particularly when the peptide of interest is rather short, normally soluble, and/or subject to proteolytic degradation within the host cell. Production of the peptide in insoluble form both facilitates simple recovery and protects the peptide from the undesirable proteolytic degradation. One means to produce the peptide in insoluble form is to recombinantly produce the peptide as part of an insoluble fusion peptide/protein by including in the fusion peptide at least one solubility tag (i.e., an inclusion body tag) that induces inclusion body formation. Typically, the fusion protein is designed to include at least one cleavable peptide linker so that the peptide of interest can be subsequently recovered from the fusion protein. The fusion protein may be designed to include a plurality of inclusion body tags, cleavable peptide linkers, and regions encoding the peptide of interest.

Fusion proteins comprising a peptide tag that facilitate the expression of insoluble proteins are well known in the art. Typically, the tag portion of the chimeric or fusion protein is large, increasing the likelihood that the fusion protein will be insoluble. Example of large peptide tides typically used include, but are not limited to chloramphenicol acetyltransferase (Dykes et al., Eur. J. Biochem., 174:411 (1988), □-galactosidase (Schellenberger et al., Int. J. Peptide Protein Res., 41:326 (1993); Shen et al., Proc. Nat. Acad. Sci. USA 281: 4627 (1984); and Kempe et al., Gene, 39:239 (1985)), glutathione-S-transferase (Ray et al., Bio/Technology, 11:64 (1993) and Hancock et al. (WO94/04688)), the N-terminus of L-ribulokinase (U.S. Pat. No. 5,206,154 and Lai et al., Antimicrob. Agents & Chemo., 37:1614 (1993), bacteriophage T4 gp55 protein (Gramm et al., Bio/Technology, 12:1017 (1994), bacterial ketosteroid isomerase protein (Kuliopulos et al., J Am. Chem. Soc. 116:4599 (1994) and in U.S. Pat. No. 5,648, 244), ubiquitin (Pilon et al., Biotechnol. Prog., 13:374-79 (1997), bovine prochymosin (Haught et al., Biotechnol. Bioengineer. 57:55-61 (1998), and bactericidal/permeability-increasing protein ("BPI"; Better, M. D. and Gavit, P D., U.S. Pat. No. 6,242,219). The art is replete with specific examples of this technology, see for example U.S. Pat. No. 6,613,548, describing fusion protein of proteinaceous tag and a soluble protein and subsequent purification from cell lysate; U.S. Pat. No. 6,037,145, teaching a tag that protects the expressed chimeric protein from a specific protease; U.S. Pat. No. 5,648, 244, teaching the synthesis of a fusion protein having a tag and a cleavable linker for facile purification of the desired protein; and U.S. Pat. Nos. 5,215,896; 5,302,526; 5,330,902; and U.S. Patent Application Publication No. 2005/221444, describing fusion tags containing amino acid compositions specifically designed to increase insolubility of the chimeric protein or peptide.

A solubility tag (~125 AA in length) derived from the ketosteroid isomerase (KSI) has been shown to be very effective in inducing inclusion body formation when fused to a small peptide of interest (pET31b(+); available from Novagen, Madison, Wis.; Kuliopulos and Walsh (1994) *J. Amer. Chem. Soc.* 116:4599-4607; U.S. Pat. No. 5,648,244). Modified derivatives of the KSI solubility tag (e.g. KSI(C4)) have been reported (U.S. Patent Application Publication Nos. 2007/0067924, 2007/0065387, 2008/0175798, 2008/0280810 and 2008/0107614 and U.S. Pat. No. 7,285,264). One useful modification has been the incorporation of additional cysteines residue into the tag, providing the option of separating the tag from the peptide of interest by oxidative cross-linking (see U.S. Patent Application Publication No. 2009/0043075.

Fusion constructs comprising the KSI(C4) solubility tag linked to a peptide of interest (POI) typically include at least one acid labile aspartic acid—proline moiety(DP moiety) separating the solubility tag from the POI. Upon treatment under suitable acid cleavage conditions, the fusion peptide is cleaved into a mixture of inclusion body tags and peptides of interest. Once cleaved, the desired peptide of interest is purified and/or partially-purified from the mixture using any number of separation techniques. Acid cleavage is a simple and cost effective means to separate the POI from the remaining portion of the fusion peptide.

However, the acid cleavage step often cleaves the KSI(C4) tag at one or more of the naturally-occurring aspartic acid residues (5 in all), often making subsequence isolation and/or purification of the POI often more difficult and/or time-consuming.

The problem to be solved is to provide an acid-resistant solubility tag that is effective in preparing insoluble fusion proteins comprising a peptide of interest.

SUMMARY OF THE INVENTION

A solubility tag is provided characterized by an increase in acid resistance. The five aspartic acid residues of KSI(C4) were replaced with glutamic acid (D→E),creating the more acid resistant solubility tag KSI(C4)E. The amino acid substitutions did not alter the peptide tag's ability to induce inclusion body formation. The KSI(C4)E tag is useful for synthesizing fusion proteins for increased expression and simple purification of short peptides ("peptides of interest"). Accordingly, the invention provides an inclusion body tag comprising the amino acid sequence SEQ ID NO: 2.

In another embodiment, a fusion peptide is provided comprising the acid-resistant inclusion body tag coupled/operably linked to a peptide of interest (POI). In a preferred embodiment, the present inclusion body tag is coupled to the peptide of interest by at least once cleavable peptide linker sequence (CS).

In another embodiment, the peptide of interest comprises one or more peptides identified and isolated from a combinatorially-generated library of peptides using a process selected from the group consisting of phage display, ribosome display, and mRNA-display.

In another embodiment, the peptide of interest comprises at least one target surface-binding peptide selected from the group consisting of hair-binding peptides, nail-binding peptides, skin-binding peptides, teeth-binding peptides, polymer-binding peptides, clay-binding peptides, antimicrobial peptides, pigment-binding peptides, and cellulose-binding peptides.

In a further embodiment, the invention provides a method for expressing a peptide of interest in an insoluble form comprising:

a) synthesizing a genetic construct encoding a fusion peptide comprising a first portion encoding the present inclusion body tag operably linked to a second portion encoding a peptide of interest;

b) transforming a microbial host cell with the genetic construct of (a);

c) growing the transformed microbial host cell of (b) under conditions wherein the genetic construct is expressed and the encoded fusion peptide is produced in an insoluble form; and d) recovering said fusion peptide in said insoluble form.

In another embodiment, a method for the production of a peptide of interest is provided comprising:

a) synthesizing a genetic construct encoding a fusion peptide comprising a first portion comprising the present inclusion body tag operably linked to a second portion comprising a peptide of interest; wherein said first portion and said second portion are separated by at least one acid-cleavable peptide linker;

b) transforming a microbial host cell with the genetic construct of (a);

c) growing the transformed microbial host cell of (b) under conditions wherein the genetic construct is expressed and the encoded fusion peptide is produced in an insoluble form;

d) recovering the fusion peptide in said insoluble form;

e) cleaving said at least one acid-cleavable peptide linker whereby said first portion of the fusion peptide is no longer fused to said second portion; and f) recovering said peptide of interest.

In another embodiment, an isolated nucleic acid molecule encoding the KSI(C4)E solubility tag of SEQ ID ON: 2 is provided.

In another embodiment, the invention provides a genetic construct encoding a fusion peptide comprising the present inclusion body tag coupled at least one peptide of interest.

In yet another embodiment, the invention provides expression vectors and microbial host cells comprising the present genetic construct.

BRIEF DESCRIPTION OF THE FIGURES

FIG. 1 is a CLUSTALW alignment of the inclusion body tags KSI(C4) and KSI(C4)E.

BRIEF DESCRIPTION OF THE BIOLOGICAL SEQUENCES

Figure 2:
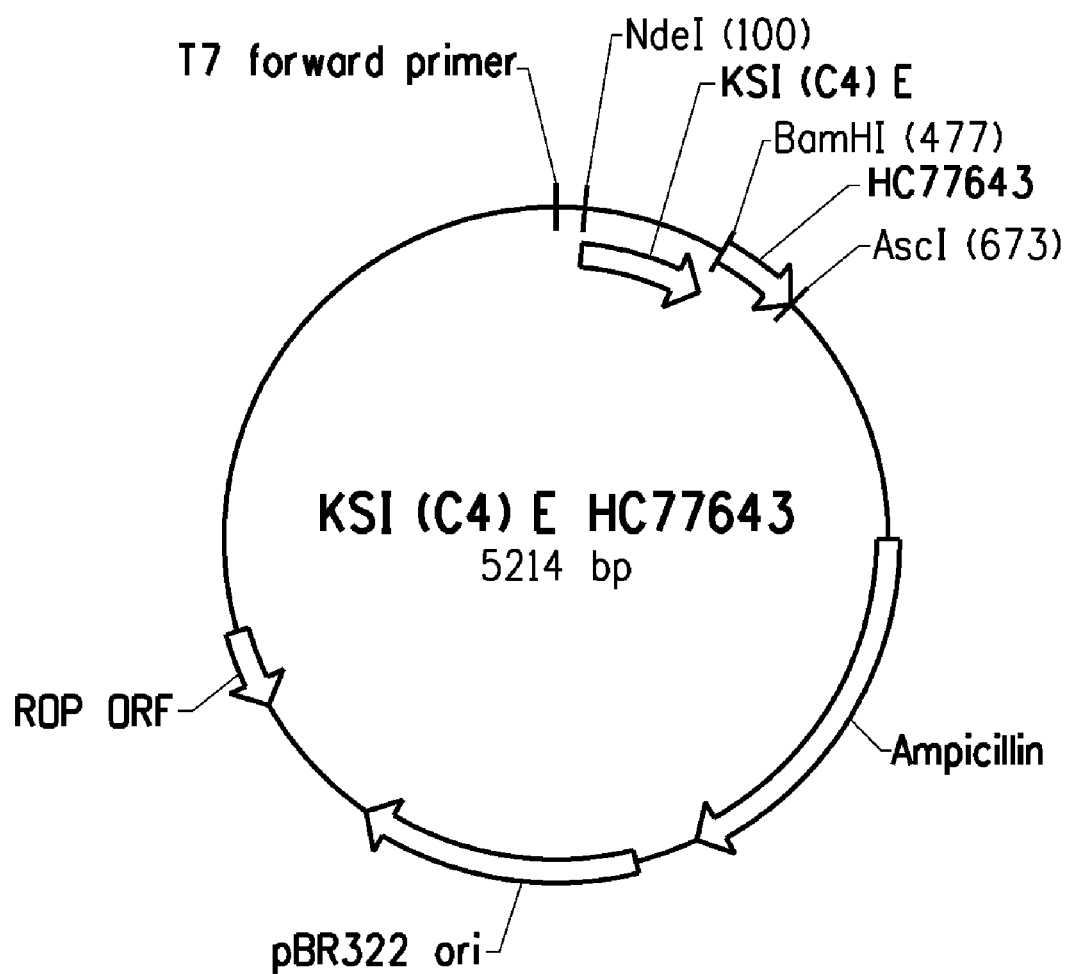
FIG. 2 is a plasmid map of pKSI(C4)E.HC77643.

The following sequences comply with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPC and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO: 1 is the nucleic acid sequence encoding KSI (C4)E.

SEQ ID NO: 2 is the amino acid sequence of KSI(C4)E.

SEQ ID NO: 3 is the nucleic acid sequence encoding KSI (C4).

SEQ ID NO: 4 is the amino acid sequence of KSI(C4).

SEQ ID NO: 5 is the nucleic acid sequence of hair-binding peptide HC77643.

SEQ ID NO: 6 is the amino acid sequence of hair-binding peptide HC77643.

SEQ ID NO: 7 is the nucleic acid sequence of plasmid pKSI(C4)E.HC77643.

SEQ ID NOs: 6 and 8-97 are the amino acid sequences of hair binding peptides.

SEQ ID NOs: 98-105 are the amino acid sequences of skin binding peptides.

SEQ ID NOs: 106-107 are the amino acid sequences of nail-binding peptides.

SEQ ID NOs: 108-136 are the amino acid sequences of antimicrobial peptides.

SEQ ID NOs: 137-161 are the amino acid sequences of pigment binding peptides. Specifically, SEQ ID NOs: 137-140 bind to carbon black, SEQ ID NOs: 141-149 bind to CROMOPHTAL® yellow (Ciba Specialty Chemicals, Basel, Switzerland), SEQ ID NOs: 150-152 bind to SUNFAST® magenta (Sun Chemical Corp., Parsippany, N.J.), and SEQ ID NOs: 153-161 bind to SUNFAST® blue.

SEQ ID NOs: 162-167 are cellulose-binding peptides.

SEQ ID NOs: 168-195 are the amino acid sequences of polymer binding peptides. Specifically, SEQ ID NO: 168 binds to poly(ethylene terephthalate), SEQ ID NOs: 169-180 bind to poly(methyl methacrylate), SEQ ID NOs: 181-186 bind to Nylon, and SEQ ID NOs: 187-195 bind to poly(tetrafluoroethylene).

SEQ ID NOs: 196-211 are the amino acid sequences of clay binding peptides.

SEQ ID NO: 212 is the amino acid sequence of the Caspase-3 cleavage sequence.

SEQ ID NOs: 213-228 are the amino acid sequences of potential acid cleavage products obtained from KSI(C4) (SEQ ID NO: 4) after acid cleavage.

SEQ ID NOs: 229-268 are the amino acid sequences of teeth-binding peptides (U.S. patent application Ser. No. 11/877,692).

DETAILED DESCRIPTION OF THE INVENTION

An acid-resistant inclusion body tag (solubility tag) is provided. The inclusion body tag acid is useful in producing a peptide of interest in the form of an insoluble fusion peptide. The fusion peptide, so assembled, is expressed in an insoluble form and is accumulated in inclusion bodies in the expressing host cell. At least one acid cleavable peptide linker (DP-cleavage site) separates the inclusion body tag from the peptide of interest.

The present inclusion body tag is useful for the expression and recovery of any bioactive peptides and proteins that are recombinantly expressed in a suitable microbial host cell. Such proteins typically have high value in any number of applications including, but not limited to medical, biomedical, diagnostic, personal care, and affinity applications where the peptides of interest are used as linkers between various surfaces.

The following definitions are used herein and should be referred to for interpretation of the claims and the specification.

The term "invention" or "present invention" as used herein is a non-limiting term and is not intended to refer to any single embodiment of the particular invention but encompasses all possible embodiments as described in the specification and the claims.

As used herein, the term "comprising" means the presence of the stated features, integers, steps, or components as referred to in the claims and does not preclude the presence or addition of one or more other features, integers, steps, components or groups thereof.

As used herein, the term "about" modifying the quantity of an ingredient or reactant of the invention employed refers to variation in the numerical quantity that can occur, for example, through typical measuring and liquid handling procedures used for making concentrates or working solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

As used herein, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As used herein, the term "pigment" refers to an insoluble, organic or inorganic colorant. In one embodiment, the pigment is a cosmetically acceptable pigment suitable for use in personal care products. In another embodiment, the peptide of interest comprises at least one first binding domain having affinity for a pigment or polymer coated pigment particle and at least one second binding domain having affinity for a body surface (e.g. hair, skin, nail, teeth, etc.) whereby the peptide of interest is capable of non-covalently coupling the pigmented particle to the desired body surface.

As used herein, the term "hair" as used herein refers to mammalian or human hair, eyebrows, and eyelashes.

As used herein, "HBP" means hair-binding peptide. As used herein, the term "hair-binding peptide" refers to peptide sequences that bind with high affinity to hair. Examples of hair binding peptides have been reported (U.S. Patent Application Publication No. 2005-0226839 to Huang et al.; WO 0179479; U.S. Patent Application Publication No. 2002/0098524 to Murray et al.; Janssen et al., U.S. Patent Application Publication No. 2003/0152976 to Janssen et al.; WO 2004048399; U.S. Patent Application Publication Nos. 2007/0067924 and 2007/0249805). Hair-binding peptides may include one or more hair-binding domains. As used herein, hair-binding peptides comprising of a plurality of hair-binding domains are referred to herein as "multi-block" or "multi-copy" hair-binding peptides. Examples of hair-binding peptides are provided herein as SEQ ID NOs: 6 and 8-97.

As used herein, the term "skin" as used herein refers to mammalian or human skin, or substitutes for human skin, such as pig skin, VITRO-SKIN® (Innovative Measurement Solutions Inc., Milford, Conn.) and EPIDERM™ (MatTek Corporation, Ashland, Mass.). Skin, as used herein, will refer to a body surface generally comprising a layer of epithelial cells and may additionally comprise a layer of endothelial cells.

As used herein, "SBP" means skin-binding peptide. As used herein, the term "skin-binding peptide" refers to peptide sequences that bind with high affinity to skin. Examples of skin binding peptides have been reported in the art (U.S. Pat. No. 7,309,482 to Buseman-Williams; Rothe et. al., WO 2004/000257; and U.S. Patent Application Publication No. 2007/0249805). Examples of skin-binding peptides are provided herein as SEQ ID NOs: 98-105.

As used herein, the term "nails" as used herein refers to mammalian or human fingernails and toenails.

As used herein, "NBP" means nail-binding peptide. As used herein, the term "nail-binding peptide" refers to peptide sequences that bind with high affinity to the surface of fingernail or toenail tissue. Examples of nail binding peptides have been reported in the art (U.S. Patent Application Publication No. 2007/0249805). Examples of nail-binding peptides are provided as SEQ ID NOs: 106-107.

As used herein, "TBP" means tooth-binding peptide. A tooth-binding peptide is a peptide that binds with high affinity to a mammalian or human tooth surface.

The term "tooth surface" will refer to a surface comprised of tooth enamel (typically exposed after professional cleaning or polishing) or tooth pellicle (an acquired surface comprising salivary glycoproteins). Hydroxyapatite can be coated with salivary glycoproteins to mimic and serve as a natural tooth pellicle surface for biopanning (tooth enamel is predominantly comprised of hydroxyapatite).

As used herein, the terms "pellicle" and "tooth pellicle" will refer to the thin film (typically ranging from about 1 μm to about 200 μm thick) derived from salivary glycoproteins which forms over the surface of the tooth crown. Daily tooth brushing tends to remove a portion of the pellicle surface while abrasive tooth cleaning and/or polishing (typically by a dental professional) will exposure more of the tooth enamel surface.

As used herein, the terms "enamel" and "tooth enamel" will refer to the highly mineralized tissue which forms the outer layer of the tooth. The enamel layer is composed primarily of crystalline calcium phosphate (i.e. hydroxyapatite; $Ca_5(PO_4)_3OH$) along with water and some organic material. In one embodiment, the tooth surface is selected from the group consisting of tooth enamel and tooth pellicle.

As used herein, the term "tooth-binding peptide" will refer to a peptide that binds to tooth enamel and/or tooth pellicle. In one embodiment, the tooth-binding peptides are from about 7 amino acids to about 50 amino acids in length, more preferably, from about 7 amino acids to about 25 amino acids in length, most preferably from about 7 to about 20 amino acids in length. In a preferred embodiment, the tooth-binding peptides are combinatorially-generated peptides.

Examples of tooth-binding peptides having been disclosed in co-pending and co-owned U.S. Patent Application Publication No. 2008/0280810. In a Preferred embodiment, the tooth-binding peptide is selected from the group consisting of SEQ ID NOs: 229-268.

As used herein, "PBP" means polymer-binding peptide. As used herein, the term "polymer-binding peptide" refers to peptide sequences that bind with high affinity to a specific polymer (U.S. pat. No. 7,427,656). Examples include peptides that bind to poly(ethylene terephthalate) (SEQ ID NO: 168), poly(methyl methacrylate) (SEQ ID NOs: 169-180), Nylon (SEQ ID NOs: 181-186), and poly(tetrafluoroethylene) (SEQ ID NOs: 187-195).

As used herein, an "antimicrobial peptide" is a peptide having the ability to kill microbial cell populations (U.S. pat. No. 7,427,656). Examples of antimicrobial peptides are provided as SEQ ID NOs: 108-136.

As used herein, "cellulose-binding peptide" refers to a peptide that binds with high affinity to cellulose. Examples of cellulose-binding peptides are provided as SEQ ID NOs: 162-167.

As used herein, "clay-binding peptide" refers to a peptide that binds with high affinity to clay (U.S. Patent Application Publication No. 2007/0249805). Examples of clay-binding peptides are provided as SEQ ID NOs: 196-211.

As used herein, "multi-block peptides" refers to a peptide comprising at least two binding moieties. Each binding moiety has an affinity (i.e. non-covalent binding) for a target substrate (e.g. hair, skin, a pigment, etc). The binding moieties may have an affinity for the same or different substrates (for example, a hair-binding moiety fused to a pigment binding moiety for targeted delivery of a pigment to hair or a peptide having a plurality of hair-binding moieties). An example of a multi-block hair-binding peptide is provided herein as HC77643 (SEQ ID NO: 6). HC77643 has been previously reported and comprises multiple hair binding domains separated by short peptide linkers.

As used herein, the "benefit agent" refers to a molecule that imparts a desired functionality to a peptide complex involving the peptide of interest for a defined application. The benefit agent may be the peptide of interest itself or may be one or more molecules bound to (covalently or non-covalently), or associated with, the peptide of interest wherein the binding affinity of the polypeptide is used to selectively target the benefit agent to the targeted material. In another embodiment, the targeted polypeptide comprises at least one region having an affinity for at least one target material (e.g., polymers, biological molecules, hair, skin, nail, teeth, other biological surfaces, other peptides, etc.) and at least one region having an affinity for the benefit agent (e.g., pharmaceutical agents, particulate benefit agents, clays, calcium carbonate, pigments, conditioners, dyes, fragrances, and polymeric coatings applied to particulate benefit agents). In another embodiment, the peptide of interest comprises a plurality of regions having an affinity for the target material and a plurality of regions having an affinity for the benefit agent. In yet another embodiment, the peptide of interest comprises at least one region having an affinity for a targeted material and a plurality of regions having an affinity for a variety of benefit agents wherein the benefit agents may be the same of different. Examples of benefits agents may include, but are not limited to conditioners for personal care products, particulate benefit agents (e.g. clays), pigments, dyes, whiteners, fragrances, pharmaceutical agents (e.g., targeted delivery of disease treatment agents), diagnostic/labeling agents, ultraviolet light blocking agents (i.e., active agents in sunscreen protectants), and antimicrobial agents (e.g., antimicrobial peptides), to name a few.

As used herein, an "inclusion body" is an intracellular amorphous deposit comprising aggregated protein found in the cytoplasm of a cell. Peptides of interest that are soluble with the host cell and/or cell lysates can be fused to one or more inclusion body tags to facilitate formation of an insoluble fusion protein. In an alternative embodiment, the peptide of interest may be partially insoluble in the host cell, but produced at relatively lows levels where significant inclusion body formation does not occur. As such, the formation of inclusion bodies will increase protein yield and/or protect the peptide from proteolytic degradation. Formation of the inclusion body facilitates purification of the fusion peptide from the cell lysate using techniques well known in the art such as centrifugation and filtration. The fusion peptide ("chimeric peptide") is designed to include one or more cleavable peptide linkers (encoding a cleavage site) separating the portion(s) comprising the peptide(s) of interest from the portion(s) comprising the present inclusion body tag. The cleavable peptide linker is designed so that the portion comprising the present inclusion body tag and the portion comprising the peptide of interest can be separated by cleaving fusion peptide at the desired cleavage site (CS). The cleavage site can be cleaved chemically (e.g., acid hydrolysis) or enzymatically (i.e., use of a protease/peptidase that preferentially recognizes an amino acid cleavage site and/or sequence within the cleavable peptide linker). Once the fusion peptide is cleaved, the inclusion body tag(s) can be separated from the peptide of interest. In one embodiment, oxidative cross-linking is used to selectively separate the inclusion body tag(s) from the peptide(s) of interest.

As used herein, the term "inclusion body tag" will be abbreviated "IBT" and will refer a polypeptide that facilitates formation of inclusion bodies when fused to a peptide of interest. The peptide of interest is typically soluble under normal physiological conditions when not fused to an inclusion body tag. Fusion of the peptide of interest to the inclusion body tag produces a fusion protein that agglomerates into intracellular bodies (inclusion bodies) within the host cell.

As used herein, "cleavable linker elements", "peptide linkers", "cleavable peptide linkers", and "cleavage site" will be used interchangeably and refer to cleavable peptide segments located between the inclusion body tag and the peptide of interest. After the inclusion bodies are separated and/or partially-purified or purified from the cell lysate, the fusion peptide is subjected to an acid cleavage step whereby the acid cleavable moiety (DP moiety) is cleaved. The cleavable peptide linker may be from 1 to about 50 amino acids, preferably from 1 to about 20 amino acids in length. In a preferred embodiment, the cleavage site is an acid cleavable aspartic acid—proline dipeptide (D-P) moiety. In an alternative embodiment, an enzymatically cleavable peptide linker may be used. For example, an enzymatically cleavable peptide linker is provided by SEQ ID NO: 212 (Caspase-3 cleavage sequence). In a preferred embodiment, the cleavage site is an acid cleavable aspartic acid—proline dipeptide (D-P) moiety. The cleavable peptide linkers may be incorporated into the fusion proteins using any number of techniques well known in the art.

As used herein, the terms "effective number of cysteine residues" and "effective number of cross-linkable cysteine residues" are used to describe the number of cysteine residues required to obtain oxidative cross-linking when the IBTs are subjected to oxidizing conditions (see U.S. Patent Application Publication No. 2009/0043075). One of skill in the art will recognize that the use of oxidative cross-linking to selectively precipitate the IBT from the POI (post cleavage of the fusion peptide) will require a POI that is devoid of cross-linkable cysteine residues. The present inclusion body tag, KSI(C4)E comprises an effective number (e.g. 4) of cross-linkable cysteine residues.

As used herein, the terms "cross-linking", "oxidative cross-linking", and "cysteine cross-linking" refers to the process of cross-linking the thiol groups of cysteine residues (i.e. forming intermolecular and intramolecular disulfide bonds) under oxidizing conditions. By definition, the formation of intermolecular disulfide bonds occurs between two or more molecules (i.e. a "plurality") comprising an effective number cross-linkable cysteine residues. As used herein, a "plurality" of molecules will alternatively be referred to herein as a "population" of molecules. In order to promoter intermolecular cross-linking, the inclusion body tag comprises an effective number (i.e. at least 3) cross-linkable cysteine residues. The present acid resistant tag comprises an effective number of cross-linkable cysteine residues (i.e., 4). Oxidative cross-linking is useful to selectively cross-link the population inclusion body tag(s) from the mixture of IBTs and POIs created after the cleavage step (with the proviso that the portion comprising the POI is devoid of cross-linkable cysteine residues).

As used herein, the term "oxidizing conditions" refers to reaction conditions which favor and promoter the formation of disulfide bonds between cysteine residues. Disulfide bond formation can be induced by any number of means well known in the art including, but not limited to contacting the cross-linkable cysteine residues with a gas comprised of oxygen (i.e. diatomic and/or triatomic oxygen) and/or the addition of chemical oxidants. The use of gas comprising molecular oxygen is preferred. In a further embodiment, a gas comprising diatomic and/or triatomic oxygen is bubbled and/or sparged through the aqueous reaction solution for a period of time to achieve effective oxidative cross-linking. The oxidative cross-linking step may optionally include the act of mixing and /or stirring of the aqueous reaction mixture for optimal results. Examples of chemical oxidants are well-known in the art and may include, but are not limited to peroxide compounds, hypochlorite, halogens, and permanganate salts; to name a few.

As used herein, the term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). In a further embodiment, the definition of "operably linked" may also be extended to describe the products of chimeric genes, such as fusion peptides. As such, "operably linked" or "coupled" will also refer to the linking of at least one copy of the present inclusion body tag to a peptide of interest to be produced and recovered.

As used herein, the terms "fusion protein", "fusion peptide", "chimeric protein", and "chimeric peptide" will be used interchangeably and will refer to a polymer of amino acids (peptide, oligopeptide, polypeptide, or protein) comprising at least two portions, each portion comprising a distinct function. At least one first portion of the fusion peptide comprises at least one copy of the present inclusion body tag. At least one second portion of the fusion peptide comprises at least one peptide of interest. The fusion peptide is designed so that an acid cleavable peptide sequence separates said at least one first portion and said at least one second portion. In a further embodiment, the fusion peptide comprises the present inclusion body tag and one or more peptides of interest where each functional portion (the IBT and the plurality of POIs) is separated by an acid cleavable peptide sequence.

Means to prepare the present peptides (inclusion body tags, cleavable peptide linkers, peptides of interest, spacer peptides, and fusion peptides) are well known in the art (see, for example, Stewart et al., Solid Phase Peptide Synthesis, Pierce Chemical Co., Rockford, Ill., 1984; Bodanszky, *Principles of Peptide Synthesis*, Springer-Verlag, New York, 1984; and Pennington et al., *Peptide Synthesis Protocols*, Humana Press, Totowa, N.J., 1994). The various components of the fusion peptides (inclusion body tag, peptide of interest, and the cleavable linker/cleavage sequence) described herein can be combined using carbodiimide coupling agents (see for example, Hermanson, Greg T., *Bioconjugate Techniques*, Academic Press, New York (1996)), diacid chlorides, diisocyanates and other difunctional coupling reagents that are reactive to terminal amine and/or carboxylic acid groups on the peptides. However, chemical synthesis is often limited to peptides of less than about 50 amino acids length due to cost and/or impurities. In a preferred embodiment, the biological molecules (IBTs, POIs, fusion peptides, etc.) described herein are prepared using standard recombinant DNA and molecular cloning techniques.

As used herein, the terms "polypeptide" and "peptide" will be used interchangeably to refer to a polymer of two or more amino acids joined together by a peptide bond, wherein the peptide is of unspecified length, thus, peptides, oligopeptides, polypeptides, and proteins are included within the present definition. In one aspect, this term also includes post expression modifications of the polypeptide, for example, glycosylations, acetylations, phosphorylations and the like. Included within the definition are, for example, peptides containing one or more analogues of an amino acid or labeled amino acids and peptidomimetics. In a preferred embodiment, the present IBTs are comprised of L-amino acids.

As used herein, the terms "protein of interest", "polypeptide of interest", "peptide of interest", "targeted protein", "targeted polypeptide", "targeted peptide", "expressible protein", and "expressible polypeptide" will be abbreviated as "POI" and will be used interchangeably and refer to a protein, polypeptide, or peptide that is bioactive and may be expressed by the genetic machinery of a host cell. In one embodiment, the peptide of interest is typically no more than 300 amino acids in length, preferably less than 100 amino acids in length, and most preferably less than 50 amino acids in length. In another embodiment, the peptide of interest is a peptide selected from a combinatorially generated library wherein the peptide is selected based on a specific affinity for a target substrate. In a further embodiment, the peptide of interest comprises one or more target surface-binding peptides (i.e. a body surface-binding peptide selected from the group consisting of hair-binding peptides, skin-binding peptides, nail-binding peptides, and teeth-binding peptides; a polymer binding peptide; a pigment-binding peptide; cellulose-binding peptide; etc.) isolated from an appropriate combinatorially-generated library of peptides using a process selected from the group consisting of phage display, ribosome display, and mRNA-display.

As used herein, the term "bioactive" or "peptide of interest activity" refers to the activity or characteristic associated with the peptide and/or protein of interest. The bioactive peptides may be used in a variety of applications including, but not limited to curative agents for diseases (e.g., insulin, interferon, interleukins, anti-angiogenic peptides (U.S. Pat. No. 6,815,426), and polypeptides that bind to defined cellular targets (with the proviso that the peptide of interest is not an antibody, an scFv antibody or the $F_{ab}$ fragment of an antibody) such as receptors, channels, lipids, cytosolic proteins, and membrane proteins, to name a few), peptides having antimicrobial activity, peptides having an affinity for a particular material (e.g., hair-binding peptides, skin-binding peptides, nail-binding peptides, teeth-binding peptides, cellulose-binding peptides, polymer-binding peptides, clay-binding peptides, and peptides that have an affinity for particular animal or plant tissues and/or proteins) targeted delivery of benefit agents.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

As used herein, the term "solubility" refers to the amount of a substance that can be dissolved in a unit volume of a liquid under specified conditions. In the present application, the term "solubility" is used to describe the ability of a peptide (inclusion body tag, peptide of interest, or fusion peptides) to be resuspended in a volume of solvent, such as a biological buffer. In one embodiment, the peptides targeted for production ("peptides of interest") are normally soluble in the cell and/or cell lysate under normal physiological conditions. Fusion of at least one copy of the inclusion body tags (IBT) to the target peptide results in the formation of a fusion peptide that is insoluble under normal physiological conditions, resulting in the formation of inclusion bodies. In one embodiment, the free peptide of interest is soluble in an aqueous matrix having a pH range of 5-12, preferably 6-10; and a temperature range of 5° C. to 50° C., preferably 10° C. to 40° C.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any naturally-occurring amino acid (or as defined herein) | Xaa | X |

As used herein, the term "host cell" refers to cell which has been transformed or transfected, or is capable of transformation or transfection by an exogenous polynucleotide sequence. In a preferred embodiment, the host cell is a microbial host cell. In a further preferred embodiment, the microbial host cell is a bacterial host cell.

As used herein, the term "isolated nucleic acid molecule" is a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

As used herein, the term "genetic construct" will refer to any combination of genetic elements, including without limitation, genes, regulatory elements, coding sequences, open reading frames and the like assembled within a single nucleic acid sequence and capable of effecting a particular genetic or phenotypic trait when transformed into an appropriate host.

As used herein, the terms "plasmid", "vector" and "cassette" refer to an extrachromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene or genetic construct and having elements in addition to the foreign gene or genetic construct that facilitates transformation of a particular host cell. "Expression cassette" refers to a specific vector containing a foreign gene or genetic construct and having elements in addition to the foreign gene or genetic construct that allow for enhanced expression of that gene in a foreign host.

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et. al., *Short Protocols in Molecular Biology*, $5^{th}$ Ed. Current Protocols and John Wiley and Sons, Inc., N.Y., 2002.

Acid-Resistant Inclusion Body Tag KSI(C4)E

The present inclusion body tag is a derived from a portion of the ketosteroid isomerase (KSI). A portion of this protein (the first 125 amino acids of the KSI protein) has been used as a solubility tag to induce insoluble fusion peptide production when fused to a peptide/protein of interest and is commercially available (see pET31b(+);Novagen, Madison, WI and Kuliopulos and Walsh (1994) *J. Amer. Chem. Soc.* 116:4599-4607; U.S. Pat. No. 5,648,244). Modified derivatives of the KSI solubility tag (e.g. KSI(C4); SEQ ID NO: 4) have been reported (U.S. Patent Application Publication Nos. 2007/0067924, 2007/0065387, 2008/0175798, 2008/0280810, and 2008/0107614 and U.S. Pat. No. 7,285,264).

However, the KSI(C4) inclusion body tag has 5 internal aspartic acid residues (none of which are adjacent to a proline residue) that have been found to be often sensitive (i.e. subject to unwanted cleavage) to the conditions used during the acid cleavage step. Cleavage of the inclusion body tag at these residues creates a more complex mixture of peptide fragments, which complicates and adds additional expense to the downstream POI recovery process.

As described herein, the amino acid sequence of the KSI (C4) tag has been engineered to make the tag more resistant to acid cleavage. The five aspartic acid residues were replaced with glutamic acid residues, creating KSI(C4)E (SEQ ID NO: 2; FIG. 1). The KSI(C4)E tag is more stable to acid hydrolysis than KSI(C4) (SEQ ID NO: 4). The modification did not alter the tag's ability to effectively induce inclusion body formation.

Furthermore, the present KSI(C4)E tag comprises an effective number of cross-linkable cysteine residues that may be used in an optional processing step to separate the IBT from the POI using oxidative cross-linking with the proviso that the POI is devoid of cysteine residues (see U.S. Patent Application Publication No. 2009-0043075).

Fusion Peptides

The KSI(C4)E tag can be fused to any peptide of interest for improved peptide production. In one embodiment, the peptide of interest is normally soluble under normal physiological conditions. The resulting fusion proteins/peptides are produced as insoluble inclusion bodies. Means to determine and measure inclusion body formation are well known in the art and may include techniques such as particle size measures, optical measuring techniques, and gel separation techniques (e.g., SDS-PAGE), to name a few.

In one embodiment, an insoluble fusion protein is provided comprising at least one copy of the present inclusion body tag (IBT) operably linked to a peptide of interest (POI) wherein the IBT is separated form the POI at least once cleavable peptide linker sequence (CS). In another embodiment, the cleavable peptide linker sequence is an aspartic acid—proline (Asp-Pro) moiety.

IBT-CS-POI or

POI-CS-IBT

Typically, the recombinant host cell is grown under suitable conditions whereby the fusion peptide is produced in insoluble form (i.e. inclusion bodies). The cells are subsequently lysed using any number of well-known techniques. The inclusion bodies are purified and/or partially purified from the cell lysate using any number of techniques including, but not limited to centrifugation and/or filtration.

The collected inclusion bodies are subjected to an acid cleavage treatment for a period of time to sufficient to obtain cleavage of the cleavable peptide linker sequences (i.e. the DP moieties), forming a mixture of peptide fragments comprising a population of peptides of interest and a population of inclusion body tags. The peptide of interest is isolated from the mixture of peptide fragments using any number of well known separation techniques.

Expressible Peptides of Interest

The peptide of interest ("expressible peptide" or "POI") targeted for production is one that is appreciably soluble in the host cell and/or host cell liquid lysate under normal physiological conditions. In a preferred aspect, the peptides of interest are generally short and difficult to produce in sufficient amounts due to proteolytic degradation. Fusion of the peptide of interest to at least one inclusion body forming tag creates a fusion peptide that is insoluble in the host cell and/or host cell lysate under normal physiological conditions. Production of the peptide of interest is typically increased when expressed and accumulated in the form of an insoluble inclusion body as the peptide is generally more protected from proteolytic degradation. Furthermore, the insoluble fusion protein can be easily separated from the host cell lysate using centrifugation and/or filtration.

In general, inclusion body tags can be used in a process to produce any peptide of interest that is (1) typically soluble in the cell and/or cell lysate under typical physiological conditions and/or (2) those that can be produced at significantly higher levels when expressed in the form of an inclusion body. In a preferred embodiment, the peptide of interest is appreciably soluble in the host cell and/or corresponding cell lysate under normal physiological and/or process conditions.

The length of the peptide of interest may vary as long as (1) the peptide is appreciably soluble in the host cell and/or cell lysate, and/or (2) the amount of the targeted peptide produced is significantly increased when expressed in the form of an insoluble fusion peptide/inclusion body (i.e. expression in the form of a fusion protein protect the peptide of interest from proteolytic degradation). Typically the peptide of interest is less than 300 amino acids in length, preferably less than 100 amino acids in length, more preferably less than 75 amino acids in length, even more preferably less than 50 amino acids in length, and most preferably less than 25 amino acids in length.

The function of the peptide of interest is may vary and may include, but is not limited to bioactive molecules such as curative agents for diseases (e.g., insulin, interferon, interleukins, peptide hormones, anti-angiogenic peptides, and peptides (with the proviso that the peptide is not an antibody or an $F_{ab}$ portion of an antibody) that bind to and affect defined cellular targets such as receptors, channels, lipids, cytosolic proteins, and membrane proteins; see U.S. Pat. No. 6,696,089), peptides having an affinity for a particular material (e.g., biological tissues, biological molecules, hair binding peptides (U.S. Patent Application Publication No. 2005/0226839; WO 0179479; U.S. Patent Application Publication No. 2002/0098524; U.S. Patent Application Publication No. 2003/0152976; WO 04/048399; U.S. Patent Application Publication No.2007/0067924; U.S. Pat. No.7,427,656; and U.S. Patent Application Publication No. 2007/0249805), skin binding peptides (U.S. Pat. No. 7,309,482; WO 2004/000257; U.S. Pat. No. 7,427,656; and U.S. Patent Application Publication No. 2007/0249805), nail binding peptides (U.S. Patent Application Publication No. 2005/0226839; U.S. Patent Application Publication No. 2007/0249805), cellulose binding peptides, polymer binding peptides (U.S. Patent Application Publication Nos. 2007/0265431, 2007/0264720, 2008/0207872, 2007/0141628, and U.S. Pat. No.7,632,919), and clay binding peptides (U.S. Patent Application Publication No. 2007/0249805), for targeted delivery of at least one benefit agent (see U.S. Pat. No. 7,220,405 and U.S. Patent Application Publication Nos. 2005/0226839 and 2007/0249805).

In a preferred embodiment, the peptide of interest is a short affinity peptide having specific affinity for a target substrate. In a further preferred embodiment, the affinity peptide is a non-naturally occurring peptide identified from a combinatorially-generated library. The combinatorially-generated peptide may be identified using any number of well-known techniques such as phage display, ribosome display, and mRNA-display, to name a few.

Affinity peptides are particularly useful to target benefit agents imparting a desired functionality to a target material (e.g., hair, skin, etc.) for a defined application (U.S. Pat. No. 7,220,405; U.S. Patent Application Publication No. 2005/0226839; and U.S. Patent Application Publication Nos. 2007/0067924 and 2007/0249805 for a list of typical benefit agents such as conditioners, pigments/colorants, fragrances, etc.). The benefit agent may be peptide of interest itself or may be one or more molecules bound to (covalently or non-covalently), or associated with, the peptide of interest wherein the binding affinity of the peptide of interest is used to selectively target the benefit agent to the targeted material. In another embodiment, the peptide of interest comprises at least one region having an affinity for at least one target material (e.g., biological molecules, polymers, hair, skin, nail, other peptides, etc.) and at least one region having an affinity for the benefit agent (e.g., pharmaceutical agents, antimicrobial agents, pigments, conditioners, dyes, fragrances, etc.). In another embodiment, the peptide of interest comprises a plurality of regions having an affinity for the target material and a plurality of regions having an affinity for one or more benefit agents. In yet another embodiment, the peptide of interest comprises at least one region having an affinity for a targeted material and a plurality of regions having an affinity for a variety of benefit agents wherein the benefit agents may be the same of different. Examples of benefits agents may include, but are not limited to conditioners for personal care products, pigments, dye, fragrances, pharmaceutical agents (e.g., targeted delivery of cancer treatment agents), diagnostic/labeling agents, ultraviolet light blocking agents (i.e., active agents in sunscreen protectants), and antimicrobial agents (e.g., antimicrobial peptides), to name a few.

In a further preferred aspect, the peptide of interest is selected from the group of hair-binding peptides, skin-binding peptides, nail-binding peptides, teeth-binding peptides, antimicrobial peptides, pigment-binding peptides, clay-binding peptides, and polymer-binding peptides. In another preferred aspect, the peptide of interest is selected from the group consisting of a hair-binding peptides (SEQ ID NOs: 6 and 8-97), skin-binding peptides (SEQ ID NOs: 98-105), nail-binding peptides (SEQ ID NOs: 106-107), and teeth-binding peptides (SEQ ID NOs: 229-268). In a further embodiment, the peptide of interest is a multi-block peptide comprising at least one hair-, skin-, nail- or teeth-binding domain (U.S. Pat. Nos. 7,220,405 and 7,285,264; for example HC77643 provided as SEQ ID NO: 6).

In another embodiment, the peptide of interest may also include previously peptides having antimicrobial activity (for example, SEQ ID NOs: 108-136) or an affinity for a non-biological material (for example, pigment-binding peptides as exemplified by SEQ ID NOs: 137-161; cellulose-binding peptides as exemplified by SEQ ID NOs: 162-167; polymer binding peptides [e.g., SEQ ID NO: 168 binds to poly(ethylene terephthalate), SEQ ID NOs: 169-180 bind to poly(methyl methacrylate), SEQ ID NOs: 181-186 bind to Nylon, and SEQ ID NOs: 187-195 bind to poly(tetrafluoroethylene)]; and clay-binding peptides as exemplified by SEQ ID NOs: 196-211).

Cleavable Peptide Linkers

The use of cleavable peptide linkers (i.e. cleavage sites or cleavage sequences) is well known in the art. Fusion peptides comprising the present inclusion body tags will include at least one cleavable sequence separating the inclusion body tag from the polypeptide of interest. The cleavable sequence facilitates separation of the inclusion body tag(s) from the peptide(s) of interest. In one embodiment, the cleavable sequence may be provided by a portion of the inclusion body tag and/or the peptide of interest (e.g., inclusion of an acid cleavable aspartic acid—proline moiety).

Means to cleave the peptide linkers are well known in the art and may include chemical hydrolysis, enzymatic cleavage agents, and combinations thereof. In one embodiment, one or more chemically cleavable peptide linkers are included in the fusion construct to facilitate recovery of the peptide of interest from the inclusion body fusion protein. Examples of chemical cleavage reagents include cyanogen bromide (cleaves methionine residues), N-chloro succinimide, iodobenzoic acid or BNPS-skatole [2-(2-nitrophenylsulfenyl)-3-methyl indole] (cleaves tryptophan residues), dilute acids (cleaves at aspartyl-prolyl bonds), and hydroxylamine (cleaves at asparagine-glycine bonds at pH 9.0); see Gavit, P. and Better, M., J. Biotechnol., 79:127-136 (2000); Szoka et al., DNA, 5(1):11-20 (1986); and Walker, J. M., *The Proteomics Protocols Handbook*, 2005, Humana Press, Totowa, N.J.)). In a preferred embodiment, one or more aspartic acid—proline acid cleavable recognition sites (i.e., a cleavable peptide linker comprising one or more D-P dipeptide moieties) are included in the fusion protein construct to facilitate separation of the inclusion body tag(s) form the peptide of interest. In another embodiment, the fusion peptide may include multiple regions encoding peptides of interest separated by one or more cleavable peptide linkers.

In another embodiment, one or more enzymatic cleavage sequences are included in the fusion protein construct to facilitate recovery of the peptide of interest. Proteolytic enzymes and their respective cleavage site specificities are well known in the art. In a preferred embodiment, the proteolytic enzyme is selected to specifically cleave only the peptide linker separating the inclusion body tag and the peptide of interest. Examples of enzymes useful for cleaving the peptide linker include, but are not limited to Arg-C proteinase, Asp-N endopeptidase, chymotrypsin, clostripain, enterokinase, Factor Xa, glutamyl endopeptidase, Granzyme B, Achromobacter proteinase 1, pepsin, proline endopeptidase, proteinase K, Staphylococcal peptidase 1, thermolysin, thrombin, trypsin, and members of the Caspase family of proteolytic enzymes (e.g. Caspases 1-10) (Walker, J. M., supra). An example of a cleavage site sequence is provided by SEQ ID NO: 212 (Caspase-3 cleavage site; Thornberry et al. *J. Biol. Chem.*, 272:17907-17911 (1997) and Tyas et al., *EMBO Reports*, 1 (3):266-270 (2000)).

Typically, the cleavage step occurs after the insoluble inclusion bodies and/or insoluble fusion peptides are isolated from the cell lysate. The cells can be lysed using any number of means well known in the art (e.g. mechanical and/or chemical lysis). Methods to isolate the insoluble inclusion bodies/fusion peptides from the cell lysate are well known in the art (e.g., centrifugation, filtration, and combinations thereof). Once recovered from the cell lysate, the insoluble inclusion bodies and/or fusion peptides can be treated with a cleavage agent (i.e. an acid cleavage agent) to cleave the inclusion body tag from the peptide of interest. In one embodiment, the fusion protein and/or inclusion body is diluted and/or dissolved in a suitable solvent prior to treatment with the cleavage agent. In a further embodiment, the cleavage step may be omitted if the inclusion body tag does not interfere with the activity of the peptide of interest.

After the cleavage step, and in a preferred embodiment, the peptide of interest can be separated and/or isolated from the fusion protein and the inclusion body tags based on a differential solubility of the components. Parameters such as pH, salt concentration, and temperature may be adjusted to facilitate separation of the inclusion body tag from the peptide of interest. In another embodiment, oxidative cross-linking may be used to separate the KSI(C4)E tag from the POI when the POI is devoid of cross-linkable cysteine residues (see U.S. Provisional Patent Application No. 60/951,754 entitled "Recombinant Peptide Production Using a Cross-Linkable Solubility Tag". Upon cleavage, oxidative cross-linking is used to selective cross-link the IBTs (typically insoluble). The conditions are controlled so that the cross-linked IBT is insoluble while the peptide of interest remains soluble. The soluble peptide of interest is subsequently separated from the cross-linked IBTs using a simple separation technique such as centrifugation and/or filtration.

In an optional embodiment, the peptide of interest may be further purified using any number of well known purification techniques in the art such as ion exchange, gel purification techniques, and column chromatography (see U.S. Pat. No. 5,648,244), to name a few.

Cysteine Cross-linking of the KSI(C4)E Tag

Recombinant production of fusion peptides/proteins in the form of inclusion bodies is well known in the art. Typically, the recombinant cells (comprising the fusion protein) are homogenized to release the insoluble inclusion bodies. Isolation of inclusion bodies from a cell lysate are based on well known techniques including, but not limited to centrifugation and/or filtration. The process typically involves several cycles of each process step (i.e. homogenization, centrifugation, washing etc.) for optimal processing. Washing and/or concentration adjustments using water are typically employed between each process step/cycle. The pH is adjusted, as needed, for optimal processing. In general, the following basic processing options may be used to obtain a semi-purified and/or purified inclusion body paste.

The process begins with a fermentation broth comprising a population of recombinant microbial host cells comprising insoluble fusion protein in the form of an inclusion body.

Option 1—Using initial cell separation from fermentation broth as a first step

The fermentation broth is either centrifuged or passed through a membrane filtration process to separate and recover cells containing inclusion bodies of the peptide to be recovered. Water and dissolved impurities and salts are removed. The recovered cell mass is re-suspended in water at a concentration of about 10 to about 250 g/L wet cells. The pH of the mixture is adjusted to a pH of about 9 to about 12, more preferentially about 10 to about 11 using a simple strong base like NaOH. The mixture is then cooled to about 0° to about 10° C. The mixture is passed through a mechanical high pressure homogenization device like a Mouton-Gaulin homogenizer at from about 8,000 psi (approximately 55.2 mPa) to about 25,000 psi (approximately 172 mPa), more preferentially about 10,000 psi (approximately 69.0 mPa) to about 15,000 psi (approximately 103 mPa), nominally about 12,000 psi (approximately 82.8 mPa) for several passes. The number of passes through the homogenizer may be varied as needed. In one embodiment, the number of passes through the homogenizer is about 1 to about 5, preferably 1 to 3, and most preferably about 3. The temperature of liquid during homogenization is preferably maintained at a temperature of about 0° C. to about 30° C., preferably about 0° C. to about 10° C.

After the final homogenization pass, the homogenized mixture is subjected to centrifugation and/or filtration. In a preferred embodiment, centrifugation (e.g. stacked disc centrifugation) is used to separate the insoluble inclusion bodies from the lysate. The concentration of lysed cell biomass is optionally adjusted to a lower concentration with water prior to centrifugation to 10 to 200 g/L, preferably 50 to 150 g/L, and most preferably about 75 g/L.

Differential settling of the inclusion bodies to a paste occurs and the overflow of the centrifuge contains the cell debris containing fraction. The recovered inclusion body rich paste is then re-suspended in water. The suspension is well mixed and re-centrifuged or membrane filtered to remove dissolved salts and residual contaminants. If needed, additional water washes may be used.

Option 2—Direct processing of the fermentation broth

Direct process of the fermentation broth may also be used. The process is essentially identical to Option 1, except that the fermentation broth is directly processed (no prior centrifugation and/or filtration steps used to isolate the cells prior to homogenization).

Option 3—The fermentation broth is pH adjusted before homogenization

In another embodiment, pH of the fermentation broth may be adjusted prior to homogenization. This option is similar to Option 2, except that the pH of the fermentation broth is adjusted to a pH of about 9 to about 12, more preferentially about 10 to about 11 prior to homogenization.

High pH Wash Followed by Water Wash

A high pH wash may be used to further purify the inclusion body paste. The concentrated inclusion body paste obtained after centrifugation is adjusted using a 1 M $NaHCO_3$ pH10 buffer to a final concentration of about 50 mM buffer. The suspension is mixed and centrifuged using a centrifuge (e.g. a stacked disk centrifuge) to separate the dissolved and suspended impurities from the inclusion bodies.

The inclusion body slurry is diluted and washed in water to remove the buffer. Centrifugation is repeated to isolate the washed inclusion body paste.

Cleavage and Oxidative Cross-Linking

In one embodiment, the semi-purified insoluble fusion protein (inclusion body paste) is re-suspended in water and subjected to a cleavage step whereby the fusion protein is cleaved into a mixture of free inclusion body tag(s), free peptides of interest. The mixture may also include some partially-cleaved and/or whole fusion proteins. As described previously, the fusion protein comprises one or more cleavable peptide sequences (e.g. cleavable peptide linkers) separating the inclusion body tag from the peptide of interest. The cleavable peptide linker may be cleaved enzymatically and/or chemically (e.g. acid cleavage of DP linker).

In a preferred embodiment, acid cleavage is used. The inclusion body slurry is adjusted to the desired solids concentration (typically about 25 g/L on a dry weight basis). The pH of the aqueous solution of fusion peptides is adjusted so that the acid labile D-P moieties are cleaved. A reducing agent, such as dithiothreitol (DTT, 10 mM) may also be used during acid hydrolysis to break disulfide bonds and to promote acid cleavage. Any suitable acid may be used including, but not limited to HCl, formic acid, nitric acid, sulfuric acid, phosphoric acid, citric acid, trifluoroacetic acid, and mixtures thereof. One of skill in the art can adjust the time, temperature, and pH for optimal cleavage. Typically, the acid treatment is conducted at a pH range of about 0.5 to about 3, more preferably 1.5 to 2.6, most preferably 1.8 to 2.2. The mixture is heated to a temperature of about 40° C. to about 90° C., preferably 50° C. to about 90° C., more preferably 60° C. to about 80° C., and most preferably about 70° C. The heated acidic mixture is held for a period of time from 30 minutes to 48 hours, preferably less than 24 hours, even more preferably less than 12 hours, and most preferably less than 8 hours to achieve effective cleavage.

The cleaved peptide mixture is then cooled to a temperature of about 25° C. and the pH is adjusted to about 5.1 (or the corresponding isoelectric point [pI] of the portion containing the plurality of cross-linkable cysteine residues). The pH adjusted solution is further cooled to a temperature of about 0° C. to about 20° C., more preferably about 0° C. to about 10° C., and most preferably about 5° C. and slowly agitated with a slow bubbling of filtered air to create an oxidizing environment. The mixture is allowed to cross-link and precipitate for a period of time sufficient to achieve effective cross-linking. The optimal time required for effective cross-linking step can be easily determined by one of skill in the art. Typically, the cross-linking step typically ranges in time from 5 minutes to about 48 hours, preferably 30 minutes to 24 hours, more preferably about 1 hour to about 12 hours, and most preferably about 2 to about 8 hours. The sediment (i.e. the cross-linked peptide aggregate) is separated from the supernatant by centrifugation or filtration.

The isolated supernatant containing the dissolved peptide of interest is pH adjusted as required to precipitate the peptide of interest. An organic solvent like acetone, ethanol or methanol may be used to induce precipitation of the target peptide or impurities. The mixture may be cooled to further increase precipitation. The product precipitate is then recovered by centrifugation or filtration. The precipitate may then be washed by chilled solvents or aqueous solvent mixtures. The product may be dried, re-suspended or dissolved as required for final use.

Transformation and Expression

Once the inclusion body tag has been paired with the appropriate peptide of interest, construction of cassettes and vectors that may be transformed in to an appropriate expression host is common and well known in the art. Typically, the vector or cassette contains sequences directing transcription and translation of the relevant chimeric gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Transcription initiation control regions or promoters, which are useful to drive expression of the genetic constructs encoding the fusion peptides in the desired host cell, are numerous and familiar to those skilled in the art. Virtually any promoter capable of driving these constructs is suitable for the present invention including but not limited to CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in Pichia); and lac, ara (pBAD), tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred hosts. Optionally, a termination site may be unnecessary; however, it is most preferred if included.

Preferred host cells for expression of the fusion peptides are microbial hosts that can be found broadly within the fungal or bacterial families and which grow over a wide range of temperature, pH values, and solvent tolerances. For example, it is contemplated that any of bacteria, yeast, and filamentous fungi will be suitable hosts for expression of the present nucleic acid molecules encoding the fusion peptides. Because of transcription, translation, and the protein biosynthetic apparatus is the same irrespective of the cellular feedstock, genes are expressed irrespective of the carbon feedstock used to generate the cellular biomass. Large-scale microbial growth and functional gene expression may utilize a wide range of simple or complex carbohydrates, organic acids and alcohols (i.e. methanol), saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression. Examples of host strains include, but are not limited to fungal or yeast species such as *Aspergillus, Trichoderma, Saccharomyces, Pichia, Yarrowia, Candida, Hansenula*, or bacterial species such as *Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*. Preferred bacterial host strain cell is *Escherichia, Pseudomonas*, or *Bacillus*. In a highly preferred aspect, the bacterial host strain is *Escherichia coli*.

Fermentation Media

Fermentation media must contain one or more suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, or methanol for which metabolic conversion into key biochemical intermediates has been demonstrated. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415-32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485-489 (1990)). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, preferred carbon substrates are glucose, fructose, and sucrose.

In addition to an appropriate carbon source, fermentation media must contain suitable minerals, salts, cofactors, buffers and other components, known to those skilled in the art, suitable for the growth of the cultures and promotion of the expression of the present fusion peptides.

Culture Conditions

Suitable culture conditions can be selected dependent upon the chosen production host. Typically, cells are grown at a temperature in the range of about 25° C. to about 40° C. in an appropriate medium. Suitable growth media may include common, commercially-prepared media such as Luria Bertani (LB) broth, Sabouraud Dextrose (SD) broth or Yeast medium (YM) broth. Other defined or synthetic growth media may also be used and the appropriate medium for growth of the particular microorganism will be known by one skilled in the art of microbiology or fermentation science. The use of agents known to modulate catabolite repression directly or indirectly, e.g., cyclic adenosine 2':3'-monophosphate, may also be incorporated into the fermentation medium.

Suitable pH ranges for the fermentation are typically between pH 5.0 to pH 9.0, where pH 6.0 to pH 8.0 is preferred.

Fermentations may be performed under aerobic or anaerobic conditions where aerobic conditions are generally preferred.

Industrial Batch and Continuous Fermentations

A classic batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Thomas D. Brock in *Biotechnology: A Textbook of Industrial Microbiology*, Second Edition (1989) Sinauer Associates, Inc., Sunderland, Mass. (hereinafter "Brock"), or Deshpande, Mukund V., *Appl. Biochem. Biotechnol.*, 36:227 (1992).

Although the fermentation is typically performed in batch mode, it is contemplated that the method would be adaptable to continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation.

Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using either batch, fed-batch or continuous processes and that any known mode of fermentation would be suitable.

Applicants specifically incorporate the entire contents of all cited references in this disclosure. Further, when an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "µL" means microliter(s), "mL" means milliliter(s), "L" means liter(s), "nm" means nanometer(s), "mm" means millimeter(s), "cm" means centimeter(s), "µm" means micrometer(s), "mM" means millimolar, "M" means molar, "mmol" means millimole(s), "µmol" means micromole(s), "pmol" means picomole(s), "g" means gram(s), "µg" means microgram(s), "mg" means milligram(s), "g" means the gravitation constant, "rpm" means revolutions per minute, "DTT" means dithiothreitol, and "cat#" means catalog number.

General Methods

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et. al., *Short Protocols in Molecular Biology*, 5$^{th}$ Ed. Current Protocols and John Wiley and Sons, Inc., N.Y., 2002.

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or in Brock (supra). All reagents, restriction enzymes and materials used for the growth and maintenance of bacterial cells were obtained from BD Diagnostic Systems (Sparks, Md.), Invitrogen (Carlsbad, Calif.), Life Technologies (Rockville, Md.), QIAGEN (Valencia, Calif.) or Sigma-Aldrich Chemical Company (St. Louis, Mo.), unless otherwise specified. Construction of Expression Vector pSF043

The vector pKSI(C4)-HC77623 was derived from the commercially available vector pDEST17 (Invitrogen). Construction of this vector has been previously described in co-pending U.S. patent application Ser. No. 11/389948, herein incorporated by reference. It includes sequences derived from the commercially available vector pET31 b (Novagen, Madison, Wis.) that encode a fragment of the enzyme ketosteroid isomerase (KSI; Kuliopulos, A. and Walsh, C. T., *J. Am. Chem. Soc.* 116:4599-4607 (1994) and U.S. 5,648,244). The KSI fragment used as an inclusion body tag to promote partition of the peptides into insoluble inclusion bodies in *E. coli*. The nucleic acid molecule encoding the KSI sequence from pET31 b was modified using standard mutagenesis procedures (QuickChange II, Stratagene, La Jolla, Calif.) to include three additional cysteine codons, in addition to the one cysteine codon found in the wild type KSI sequence, resulting in the inclusion body tag KSI(C4) (SEQ ID NOs: 3 and 4). The plasmid pKSI(C4)-HC77623 was constructed using standard recombinant DNA methods well known to those skilled in the art. The BamHI and AscI restriction sites facilitated swapping of nucleic acid molecules encoding the various peptides of interest. The inserts were designed to encode an acid cleavable DP moiety useful in separating the inclusion body tag from the peptide of interest.

The HC77643 (SEQ ID NOs: 5 and 6) gene was synthesized by DNA 2.0 with appropriate restriction sites on either end and cloned into the KSI(C4)-HC77623 vector as described above, creating vector pSF043.

Construction of T7-KSI(C4)E: pSF043

The nucleic acid molecule (SEQ ID NO: 1) encoding KSI (C4)E (SEQ ID NO: 2) was generated synthetically flanked by NdeI and BamHI restriction sites and delivered as plasmids harboring kanamycin resistance by DNA 2.0 (Menlo Park, Calif.). The synthetic KSI(C4)E containing plasmid (DNA 2.0) was digested in Buffer 2 (New England Biolabs 10 mM Tris-HCl, 10 mM MgCl2, 50mM NaCl, 1 mM dithiothreitol pH7.9) with the NdeI and BamHI restriction enzymes (New England Biolabs; Beverly, Mass. NdeI cat# R01 11, BamHI cat# R01 36). Likewise, the test system expression vector pSF043 was digested with NdeI and BamHI as described. The KSI(C4)E inclusion body fusion partner restriction digest was directly ligated to the NdeI/BamHI digested test expression vector pSF043 with T4 DNA Ligase (New England Biolabs; cat# M0202) at 12° C. for 18 hours. Ligation resulted in the replacement of KSI(C4) with KSI (C4)E. Only ampicillin resistant colonies were sequenced. The sequence of the expected plasmid was confirmed. The resulting expression plasmid (pLD43.KSI(C4)E; also referred to herein as pKSI(C4)E HC77643; SEQ ID NO: 7; FIG. 2), was transformed into the arabinose inducible expression strain, BL21-AI *E. Coli* strain (Invitrogen cat# C6070-03).

EXAMPLE 1

Preparation. Isolation and Processing of Fusion Protein Growth Conditions

The BL21-AI *E. coli* cells containing expression plasmids pLD43.KSI(C4)E or pSF043 were grown for 20 hours at 37° C. with agitation (200 rpm) in 2.8-L Fernbach flasks containing 1-L of modified ZYP-5052 auto-induction media (Studier, F. William, *Protein Expression and Purification*

(2005) 41 L207-234). The media composition per liter was as follows: 10 g/L Tryptone, 5 g/L Yeast Extract, 5 g/L NaCl, 50 mM $Na_2HPO_4$, 50 mM $KH_2PO_4$, 25 mM $(NH_4)_2SO_4$, 3 mM $MgSO_4$, 0.75% glycerol, 0.075% glucose and 0.05% Arabinose (inducer for BL21 AI T7 system). Under these conditions about 20 g/L wet weight of cells are obtained per liter.

Inclusion Body Isolation

The entire process was performed in one 500-mL bottle. Cells are separated from the growth media by centrifugation and washed with 200-mL (10 g cell paste/100-mL buffer) 20 mM Tris buffer and 10 mM EDTA at pH 8.0. The cell paste was resuspended in 200 mL of 20 mM Tris buffer and 10 mM EDTA at pH 8.0 with added lysozyme (5 mg/200-mL) and taken through at lease one freeze-thaw cycles to facilitate lysis. Lysis is completed by sonication and the inclusion body paste is recovered by centrifugation (9000 RCF 20 minutes 4° C.). Each additional wash step includes resuspension of the inclusion body paste, followed by sonication and centrifugation (9000 RCF 20 minutes 4° C.). Wash steps include a high pH wash (50 mM Tris HCL pH 9.0) followed by additional washes with 20 mM Tris-HCl pH 8.0. Typically 5 g/L inclusion body paste was recovered.

Acid Cleavage

The recovered inclusion body paste was resuspended in 100-mL of pure water and the pH of the mixture adjusted to 2.2 using HCl. The acidified suspension was heated to 70° C. for 14 hours with agitation to complete cleavage of the DP site separating the fusion peptide from the product peptide.

Oxidative Cross-Linking to Separate the IBT from the Peptide of Interest

The product was cooled ~5° C. then the pH neutralized to 5.3 using NaOH and cooled for an additional 1 hour at ~5° C. to facilitate precipitation of cysteine cross-linked KSI (C4)E tag. The mixture was then centrifuged at 10000 RCF for 30 minutes 4° C. The pellet contains the inclusion body fusion partner KSI (C4)E.

Results after Oxidative Cross-Linking

Figure 3A:
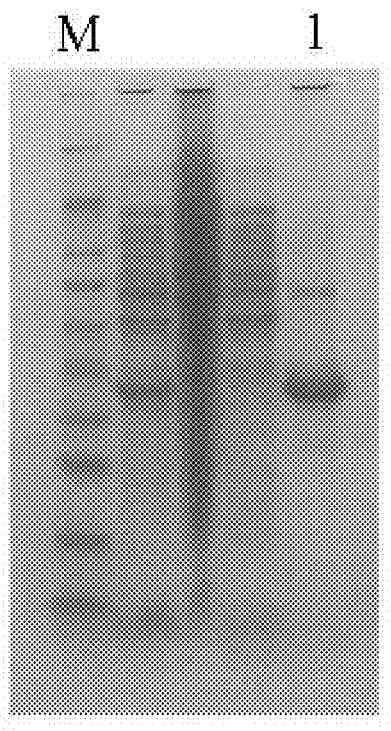
FIG. 3 are two gels denotes as 3A and 3B showing the various peptide fragments generated during the acid hydrolysis processing of KSI(C4)E.HC77643. "M" is used to designate the lanes containing the molecular weight markers. SAMPLE 1 (lane "1") is the purified Inclusion bodies KSI (C4)E.HC77643. SAMPLE 2 (lane "2") is the pool of peptide fragments obtained after the 14 hour acid hydrolysis step of the fusion peptide. SAMPLE 3 (lane "3") is the single soluble peptide band (HC77643) obtained after oxidative cross-linking of the KSI(C4)E tag. SAMPLE 4 (lane "4") is a sample of KSI(C4)E pellet obtained from oxidative cross-linking.
Figure 3B:
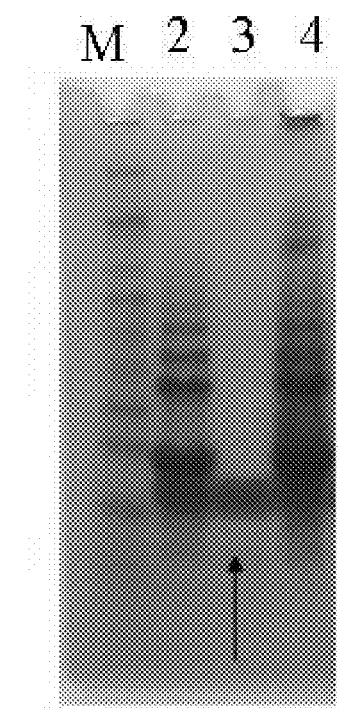

SDS-PAGE gel analysis (FIG. 3) of both the precipitate paste and the remaining soluble fraction showed the presence of KSI(C4)E in the insoluble paste (FIG. 2; lane 4) and HC77643 remaining in the soluble fraction (FIG. 2; lane 3).

The supernatant contains HC77643 and was analyzed by HPLC to confirm presence of peptide. Further analysis of isolated HC77643 by LCMS confirmed the absence of contaminating KSI fragments seen with the KSI (C4) version which contains 5 potential internal acid cleavable "D" sequence and 1 preferred acid cleavage site (Asp-Pro).

Table 1 describes 17 potential acid cleavage products for KSI (C4). All but 7 fragments have cysteine available for disulfide bond formation and are potential contaminates of the supernatant containing HC77643. Fragments with the molecular weights 3392.9, 2606.0 and 2377.7 were common contaminates of purified peptides as determined by LCMS analysis and visualized by PAGE. The other 10 fragments were routinely not seen and assumed that effective disulfide cross-linking occurred and these fragments were effectively separated from the peptide of interest during the recovery process. Use of KSI (C4)E, which replaced D→E eliminates internal acid cleavage sites and contamination of peptide with KSI (C4)E fragments. This was confirmed by LCMS and PAGE analysis.

TABLE 1

Possible KSI (C4) Fragments Obtained From Acid Cleavage

| KSI (C4) Fragment No. | Amino Acid Sequence Of Fragment | Molecular Weight | Cysteine Residue Present |
|---|---|---|---|
| KSI (C4) | MHTPEHITAVVQRFVAALNAGDLDGIVALFA DDATVEEPVGSEPRSGTAACREFYANSLKLP LAVELTQECRAVANEAAFAFTVSFEYQGRKT VVAPCDHFRFNGAGKVVSIRALFGEKNIHAC QGSD (SEQ ID NO: 4) | 13729.5 | Yes |
| 1 | MHTPEHITAVVQRFVAALNAGDLDGIVALFA D (SEQ ID NO: 213) | 3392.9 | No |
| 2 | MHTPEHITAVVQRFVAALNAGDLD (SEQ ID NO: 214) | 2606.0 | No |
| 3 | MHTPEHITAVVQRFVAALNAGD (SEQ ID NO: 215) | 2377.7 | No |
| 4 | LDGIVALFADD (SEQ ID NO: 216) | 1148.3 | No |
| 5 | LDGIVALFAD (SEQ ID NO: 217) | 1033.2 | No |
| 6 | GIVALFADD (SEQ ID NO: 218) | 920.0 | No |
| 7 | GIVALFAD (SEQ ID NO: 219) | 804.9 | No |

TABLE 1-continued

Possible KSI (C4) Fragments Obtained From Acid Cleavage

| KSI (C4) Fragment No. | Amino Acid Sequence Of Fragment | Molecular Weight | Cysteine Residue Present |
|---|---|---|---|
| 8 | MHTPEHITAVVQRFVAALNAGDLDGIVALFA DDATVEEPVGSEPRSGTAACREFYANSLKLP LAVELTQECRAVANEAAFAFTVSFEYQGRKT VVAPCDHFRFNGAGKVVSIRALFGEKNIHAC QGSD (SEQ ID NO: 4) | 13729.5 | Yes |
| 9 | LDGIVALFADDATVEEPVGSEPRSGTAACRE FYANSLKLPLAVELTQECRAVANEAAFAFTV SFEYQGRKTVVAPCDHFRFNGAGKVVSIRAL FGEKNIHACQGSD (SEQ ID NO: 220) | 11369.8 | Yes |
| 10 | GIVALFADDATVEEPVGSEPRSGTAACREFY ANSLKLPLAVELTQECRAVANEAAFAFTVSF EYQGRKTVVAPCDHFRFNGAGKVVSIRALFG EKNIHACQGSD (SEQ ID NO: 221) | 11141.5 | Yes |
| 11 | MHTPEHITAVVQRFVAALNAGDLDGIVALFA DDATVEEPVGSEPRSGTAACREFYANSLKLP LAVELTQECRAVANEAAFAFTVSFEYQGRKT VVAPCD (SEQ ID NO: 222) | 10587.9 | Yes |
| 12 | DATVEEPVGSEPRSGTAACREFYANSLKLPL AVELTQECRAVANEAAFAFTVSFEYQGRKTV VAPCDHFRFNGAGKVVSIRALFGEKNIHACQ GSD (SEQ ID NO: 223) | 10354.6 | Yes |
| 13 | LDGIVALFADDATVEEPVGSEPRSGTAACRE FYANSLKLPLAVELTQECRAVANEAAFAFTV SFEYQGRKTVVAPCD (SEQ ID NO: 224) | 8228.2 | Yes |
| 14 | GIVALFADDATVEEPVGSEPRSGTAACREFY ANSLKLPLAVELTQECRAVANEAAFAFTVSF EYQGRKTVVAPCD (SEQ ID NO: 225) | 7999.9 | Yes |
| 15 | DATVEEPVGSEPRSGTAACREFYANSLKLPL AVELTQECRAVANEAAFAFTVSFEYQGRKTV VAPCD (SEQ ID NO: 226) | 7213.0 | Yes |
| 16 | MHTPEHITAVVQRFVAALNAGDLDGIVALFA DD (SEQ ID NO: 227) | 3508.0 | Yes |
| 17 | HFRFNGAGKVVSIRALFGEKNIHACQGSD (SEQ ID NO: 228) | 3159.6 | Yes |

What is claimed is:

1. An inclusion body tag comprising the amino acid sequence of SEQ ID NO: 2.

2. A fusion peptide comprising the inclusion body tag of claim 1 fused to at least one peptide of interest.

3. The fusion peptide of claim 2 further comprising at least one cleavage site separating the inclusion body tag from the at least one peptide of interest.

4. The fusion peptide of claim 3 wherein the cleavage site is an acid cleavable aspartic acid—proline dipeptide.

5. The fusion peptide of claim 2 wherein the at least one peptide of interest is selected from the group consisting of a polymer-binding peptide, a hair-binding peptide, a nail-binding peptide, a skin-binding peptide, a teeth-binding peptide, an antimicrobial peptide, a clay-binding peptide, a pigment-binding peptide, and a cellulose-binding peptide.

6. An isolated nucleic acid molecule encoding the inclusion body tag of claim 1.

7. An isolated genetic construct encoding the fusion peptide of claim 2.

8. An expression cassette comprising the isolated genetic construct of claim 7.

9. A vector comprising the expression cassette of claim 8.

10. A microbial host cell comprising the vector of claim 9.

11. The microbial host cell of claim 10 wherein the microbial host cell is *Escherichia coli*.

12. A method for expressing and recovering a peptide of interest in an insoluble form comprising:
    a) synthesizing an expressible genetic construct encoding a fusion peptide comprising the inclusion body tag of SEQ ID NO: 2 and a peptide of interest;
    b) transforming a microbial host cell with the expressible genetic construct synthesized in (a);
    c) growing the transformed microbial host cell of (b) under conditions wherein the expressible genetic construct is expressed to produce an insoluble fusion peptide comprising the inclusion body tag of SEQ ID NO: 2 and a peptide of interest; and
    d) recovering said insoluble fusion peptide.

13. A method for the production and recovery of a peptide of interest comprising:
    a) synthesizing a genetic construct encoding a fusion peptide comprising the inclusion body tag of SEQ ID NO: 2 and at least one peptide of interest separated by at least one acid cleavable peptide linker;
    b) transforming a microbial host cell with the genetic construct synthesized in (a);
    c) growing the transformed microbial host cell of (b) under conditions wherein the genetic construct is expressed to produce an insoluble fusion peptide comprising the inclusion body tag of SEQ ID NO: 2 and a peptide of interest in an insoluble form;
    d) recovering the insoluble fusion peptide;
    e) optionally dissolving the recovered insoluble fusion peptide of (d) to produce a dissolved fusion peptide;
    f) cleaving said insoluble fusion peptide of (d) or the dissolved fusion peptide of (e) at the at least one cleavable peptide linker; and
    g) recovering said peptide of interest.

14. The method according to claim 13 wherein the acid cleavable peptide linker is an aspartic acid—proline dipeptide.

15. The method according to claim 14 wherein the peptide of interest is selected from the group consisting of a polymer-binding peptide, a hair-binding peptide, a nail-binding peptide, a skin-binding peptide, a teeth binding peptide, a clay-binding peptide, a pigment-binding peptide, a cellulose-binding peptide, and an antimicrobial peptide.

* * * * *

SEQUENCE LISTING

<160> NUMBER OF SEQ ID NOS: 268

<210> SEQ ID NO 1
<211> LENGTH: 384
<212> TYPE: DNA
<213> ORGANISM: artificial sequence
<220> FEATURE:
<223> OTHER INFORMATION: coding sequence for inclusion body tag KSI(C4)E

<400> SEQUENCE: 1
atgcacactc cagaacatat caccgcagta gtacagcgtt ttgtggcagc tctgaacgcg    60

-continued

```
ggcgagctgg aaggtattgt ggcgctgttc gcggaagaag ccaccgtgga agaaccggtg      120
ggttctgaac cgcgttccgg caccgcagcc tgccgtgaat tttacgcaaa cagcctgaag      180
ctgccgctgg cggttgaact gacccaagaa tgtcgtgcgg tggctaacga agccgctttc      240
gcgttcaccg tgtccttcga ataccagggt cgtaagaccg ttgtggcgcc atgcgaacac      300
tttcgtttca cggcgcagg caaagtggtt ccatccgcg cactgttcgg tgaaaagaac        360
atccatgctt gtcagggatc cgac                                             384
```

<210> SEQ ID NO 2
<211> LENGTH: 128
<212> TYPE: PRT
<213> ORGANISM: artificial sequence
<220> FEATURE:
<223> OTHER INFORMATION: inclusion body tag KSI(C4)E

<400> SEQUENCE: 2

```
Met His Thr Pro Glu His Ile Thr Ala Val Val Gln Arg Phe Val Ala
1               5                   10                  15

Ala Leu Asn Ala Gly Glu Leu Glu Gly Ile Val Ala Leu Phe Ala Glu
            20                  25                  30

Glu Ala Thr Val Glu Glu Pro Val Gly Ser Glu Pro Arg Ser Gly Thr
        35                  40                  45

Ala Ala Cys Arg Glu Phe Tyr Ala Asn Ser Leu Lys Leu Pro Leu Ala
    50                  55                  60

Val Glu Leu Thr Gln Glu Cys Arg Ala Val Ala Asn Glu Ala Ala Phe
65                  70                  75                  80

Ala Phe Thr Val Ser Phe Glu Tyr Gln Gly Arg Lys Thr Val Val Ala
                85                  90                  95

Pro Cys Glu His Phe Arg Phe Asn Gly Ala Gly Lys Val Val Ser Ile
            100                 105                 110

Arg Ala Leu Phe Gly Glu Lys Asn Ile His Ala Cys Gln Gly Ser Asp
        115                 120                 125
```

<210> SEQ ID NO 3
<211> LENGTH: 384
<212> TYPE: DNA
<213> ORGANISM: artificial sequence
<220> FEATURE:
<223> OTHER INFORMATION: Synthetic construct. Nucleic acid sequence
      encoding KSI(C4)

<400> SEQUENCE: 3

```
atgcataccc cagaacacat caccgccgtg gtacagcgct ttgtggctgc gctcaatgcc      60
ggcgatctga cggcatcgt cgcgctgttt gccgatgacg ccacggtgga agagcccgtg      120
ggttccgagc ccaggtccgg tacggctgcg tgtcgtgagt tttacgccaa ctcgctcaaa      180
ctgcctttgg cggtggagct gacgcaggag tgccgcgcgg tcgccaacga agcggccttc      240
gctttcaccg tcagcttcga gtatcagggc gcaagaccg tagttgcgcc ctgtgatcac       300
tttcgcttca atggcgccgg caaggtggtg agcatccgcg ccttgtttgg cgagaagaat      360
attcacgcat gccagggatc cgac                                             384
```

<210> SEQ ID NO 4
<211> LENGTH: 128
<212> TYPE: PRT
<213> ORGANISM: artificial sequence
<220> FEATURE:
<223> OTHER INFORMATION: Synthetic construct. KSI(C4)

<400> SEQUENCE: 4

Met His Thr Pro Glu His Ile Thr Ala Val Val Gln Arg Phe Val Ala
1               5                   10                  15

Ala Leu Asn Ala Gly Asp Leu Asp Gly Ile Val Ala Leu Phe Ala Asp
                20                  25                  30

Asp Ala Thr Val Glu Glu Pro Val Gly Ser Glu Pro Arg Ser Gly Thr
            35                  40                  45

Ala Ala Cys Arg Glu Phe Tyr Ala Asn Ser Leu Lys Leu Pro Leu Ala
        50                  55                  60

Val Glu Leu Thr Gln Glu Cys Arg Ala Val Ala Asn Glu Ala Ala Phe
65                  70                  75                  80

Ala Phe Thr Val Ser Phe Glu Tyr Gln Gly Arg Lys Thr Val Val Ala
                85                  90                  95

Pro Cys Asp His Phe Arg Phe Asn Gly Ala Gly Lys Val Val Ser Ile
            100                 105                 110

Arg Ala Leu Phe Gly Glu Lys Asn Ile His Ala Cys Gln Gly Ser Asp
        115                 120                 125

<210> SEQ ID NO 5
<211> LENGTH: 180
<212> TYPE: DNA
<213> ORGANISM: artificial sequence
<220> FEATURE:
<223> OTHER INFORMATION: Coding sequence for hair-binding peptide
      HC77643

<400> SEQUENCE: 5
cctggtatcc cgtggtggaa cattcgcgca cctctgaatg ctggtgctgg tattccgtgg      60
tggaacatcc gtgctcctct gaacgcgggt ggctccggtc cgggctccgg tggcaacacg     120
agccaactga gcaccggtgg tggcaacact tcccagctgt ccaccggcgg tccgaaaaag     180

<210> SEQ ID NO 6
<211> LENGTH: 60
<212> TYPE: PRT
<213> ORGANISM: artificial sequence
<220> FEATURE:
<223> OTHER INFORMATION: Hair-binding peptide HC77643

<400> SEQUENCE: 6

Pro Gly Ile Pro Trp Trp Asn Ile Arg Ala Pro Leu Asn Ala Gly Ala
1               5                   10                  15

Gly Ile Pro Trp Trp Asn Ile Arg Ala Pro Leu Asn Ala Gly Gly Ser
                20                  25                  30

Gly Pro Gly Ser Gly Gly Asn Thr Ser Gln Leu Ser Thr Gly Gly Gly
            35                  40                  45

Asn Thr Ser Gln Leu Ser Thr Gly Gly Pro Lys Lys
    50                  55                  60

<210> SEQ ID NO 7
<211> LENGTH: 5214
<212> TYPE: DNA
<213> ORGANISM: artificial sequence
<220> FEATURE:
<223> OTHER INFORMATION: plasmid

<400> SEQUENCE: 7
tacctgcctg acagcatgg cctgcaacgc gggcatcccg atgccgccgg aagcgagaag      60
aatcataatg gggaaggcca tccagcctcg cgtcgcgaac gccagcaaga cgtagcccag    120

-continued

```
cgcgtcggcc gccatgccgg cgataatggc ctgcttctcg ccgaaacgtt tggtggcggg      180
accagtgacg aaggcttgag cgagggcgtg caagattccg aataccgcaa gcgacaggcc      240
gatcatcgtc gcgctccagc gaaagcggtc ctcgccgaaa atgacccaga gcgctgccgg      300
cacctgtcct acgagttgca tgataaagaa gacagtcata agtgcggcga cgatagtcat      360
gccccgcgcc caccggaagg agctgactgg gttgaaggct ctcaagggca tcggtcgatc      420
gacgctctcc cttatgcgac tcctgcatta ggaagcagcc cagtagtagg ttgaggccgt      480
tgagcaccgc cgccgcaagg aatggtgcat gcaaggagag ggcgcccaac agtccccggg      540
ccacggggcc tgccaccata cccacgccga aacaagcgct catgagcccg aagtggcgag      600
cccgatcttc cccatcggtg atgtcggcga tataggcgcc agcaaccgca cctgtggcgc      660
cggtgatgcc ggccacgatg cgtccggcgt agaggatcga gatctcgatc ccgcgaaatt      720
aatacgactc actataggga gaccacaacg gtttccctct agaataatt ttgtttaact       780 ttaagaagga gatatacata tgcacactcc agaacatatc accgcagtag tacagcgttt      840
tgtggcagct ctgaacgcgg gcgagctgga aggtattgtg gcgctgttcg cggaagaagc      900
caccgtggaa gaaccggtgg gttctgaacc gcgttccggc accgcagcct gccgtgaatt      960
ttacgcaaac agcctgaagc tgccgctggc ggttgaactg acccaagaat gtcgtgcggt     1020
ggctaacgaa gccgctttcg cgttcaccgt gtccttcgaa taccagggtc gtaagaccgt     1080
tgtggcgcca tgcgaacact ttcgtttcaa cggcgcaggc aaagtggttt ccatccgcgc     1140
actgttcggt gaaaagaaca tccatgcctt gtcagggatcc gaccctggta tcccgtggtg     1200
gaacattcgc gcacctctga atgctggtgc tggtattccg tggtggaaca tccgtgctcc     1260
tctgaacgcg ggtggctccg gtccgggctc cggtggcaac acgagccaac tgagcaccgg     1320
tggtggcaac acttcccagc tgtccaccgg cggtccgaaa agtaataag gcgcgccgac      1380 ccagcttttct tgtacaaagt ggttgattcg aggctgctaa caaagcccga aggaagctg      1440 agttggctgc tgccaccgct gagcaataac tagcataacc ccttgggcc tctaaacggg      1500 tcttgagggg ttttttgctg aaaggaggaa ctatatccgg atatccacag gacgggtgtg     1560
gtcgccatga tcgcgtagtc gatagtggct ccaagtagcg aagcgagcag gactgggcgg     1620
cggccaaagc ggtcggacag tgctccgaga acgggtgcgc atagaaattg catcaacgca     1680
tatagcgcta gcagcacgcc atagtgactg gcgatgctgt cggaatggac gatatcccgc     1740
aagaggcccg gcagtaccgg cataaccaag cctatgccta cagcatccag ggtgacggtg     1800
ccgaggatga cgatgagcgc attgttagat tcatacacg gtgcctgact gcgttagcaa      1860
tttaactgtg ataaactacc gcattaaagc ttatcgatga taagctgtca acatgagaa      1920 ttcttgaaga cgaaagggcc tcgtgatacg cctatttta taggttaatg tcatgataat      1980
aatggtttct tagacgtcag gtggcacttt tcggggaaat gtgcgcggaa cccctatttg     2040 tttattttc taaatacatt caaatatgta tccgctcatg agacaataac cctgataaat     2100
gcttcaataa tattgaaaaa ggaagagtat gagtattcaa catttccgtg tcgcccttat     2160 tcccttttt gcggcatttt gccttcctgt ttttgctcac ccagaaacgc tggtgaaagt     2220
aaaagatgct gaagatcagt tgggtgcacg agtgggttac atcgaactgg atctcaacag     2280
cggtaagatc cttgagagtt ttcgccccga agaacgtttt ccaatgatga gcacttttaa     2340
agttctgcta tgtggcgcgg tattatcccg tgttgacgcc gggcaagagc aactcggtcg     2400
ccgcatacac tattctcaga atgacttggt tgagtactca ccagtcacag aaaagcatct     2460
```

```
tacggatggc atgacagtaa gagaattatg cagtgctgcc ataaccatga gtgataacac    2520
tgcggccaac ttacttctga caacgatcgg aggaccgaag gagctaaccg ctttttttgca   2580 caacatgggg gatcatgtaa ctcgccttga tcgttgggaa ccggagctga atgaagccat    2640
accaaacgac gagcgtgaca ccacgatgcc tgcagcaatg gcaacaacgt tgcgcaaact    2700
attaactggc gaactactta ctctagcttc ccggcaacaa ttaatagact ggatggaggc    2760
ggataaagtt gcaggaccac ttctgcgctc ggcccttccg gctggctggt ttattgctga    2820
taaatctgga gccggtgagc gtgggtctcg cggtatcatt gcagcactgg ggccagatgg    2880
taagccctcc cgtatcgtag ttatctacac gacggggagt caggcaacta tggatgaacg    2940
aaatagacag atcgctgaga taggtgcctc actgattaag cattggtaac tgtcagacca    3000
agtttactca tatatacttt agattgattt aaaacttcat ttttaattta aaaggatcta    3060
ggtgaagatc cttttgata atctcatgac caaaatccct taacgtgagt tttcgttcca     3120
ctgagcgtca gacccgtag aaaagatcaa aggatcttct tgagatcctt tttttctgcg     3180
cgtaatctgc tgcttgcaaa caaaaaaacc accgctacca gcggtggttt gtttgccgga    3240
tcaagagcta ccaactcttt ttccgaaggt aactggcttc agcagagcgc agataccaaa    3300
tactgtcctt ctagtgtagc cgtagttagg ccaccacttc aagaactctg tagcaccgcc    3360
tacatacctc gctctgctaa tcctgttacc agtggctgct gccagtggcg ataagtcgtg    3420
tcttaccggg ttggactcaa gacgatagtt accggataag gcgcagcggt cgggctgaac    3480
ggggggttcg tgcacacagc ccagcttgga gcgaacgacc tacaccgaac tgagatacct    3540
acagcgtgag ctatgagaaa gcgccacgct cccgaaggg agaaaggcgg acaggtatcc     3600
ggtaagcggc agggtcggaa caggagagcg cacgagggag cttccagggg gaaacgcctg    3660
gtatctttat agtcctgtcg ggtttcgcca cctctgactt gagcgtcgat ttttgtgatg    3720
ctcgtcaggg gggcggagcc tatggaaaaa cgccagcaac gcggcctttt tacggttcct    3780
ggccttttgc tggccttttg ctcacatgtt ctttcctgcg ttatcccctg attctgtgga    3840
taaccgtatt accgcctttg agtgagctga taccgctcgc cgcagccgaa cgaccgagcg    3900
cagcgagtca gtgagcgagg aagcggaaga gcgcctgatg cggtattttc tccttacgca    3960
tctgtgcggt atttcacacc gcatatatgg tgcactctca gtacaatctg ctctgatgcc    4020
gcatagttaa gccagtatac actccgctat cgctacgtga ctgggtcatg gctgcgcccc    4080
gacacccgcc aacacccgct gacgcgccct gacgggcttg tctgctcccg gcatccgctt    4140
acagacaagc tgtgaccgtc tccgggagct gcatgtgtca gaggttttca ccgtcatcac    4200
cgaaacgcgc gaggcagctg cggtaaagct catcagcgtg gtcgtgaagc gattcacaga    4260
tgtctgcctg ttcatccgcg tccagctcgt tgagtttctc cagaagcgtt aatgtctggc    4320
ttctgataaa gcgggccatg ttaagggcgg ttttttcctg tttggtcact gatgcctccg    4380
tgtaaggggg atttctgttc atgggggtaa tgataccgat gaaacgagag aggatgctca    4440
cgatacgggt tactgatgat gaacatgccc ggttactgga acgttgtgag ggtaaacaac    4500
tggcggtatg gatgcggcgg gaccagagaa aaatcactca gggtcaatgc cagcgcttcg    4560
ttaatacaga tgtaggtgtt ccacagggta gccagcagca tcctgcgatg cagatccgga    4620
acataatggt gcagggcgct gacttccgcg tttccagact ttacgaaaca cggaaaccga    4680
agaccattca tgttgttgct caggtcgcag acgttttgca gcagcagtcg cttcacgttc    4740
gctcgcgtat cggtgattca ttctgctaac cagtaaggca accccgccag cctagccggg    4800
tcctcaacga caggagcacg atcatgcgca cccgtggcca ggacccaacg ctgcccgaga    4860
```

```
tgcgccgcgt gcggctgctg gagatggcgg acgcgatgga tatgttctgc caagggttgg    4920
tttgcgcatt cacagttctc cgcaagaatt gattggctcc aattcttgga gtggtgaatc    4980
cgttagcgag gtgccgccgg cttccattca ggtcgaggtg gcccggctcc atgcaccgcg    5040
acgcaacgcg gggaggcaga caaggtatag gcggcgcct acaatccatg ccaacccgtt     5100
ccatgtgctc gccgaggcgg cataaatcgc cgtgacgatc agcggccag tgatcgaagt      5160 taggctggta agagccgcga gcgatccttg aagctgtccc tgatggtcgt catc           5214
```

<210> SEQ ID NO 8
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 8

Tyr Pro Ser Phe Ser Pro Thr Tyr Arg Pro Ala Phe
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 9

Ala Leu Pro Arg Ile Ala Asn Thr Trp Ser Pro Ser
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Hair Binding Peptide Domain

<400> SEQUENCE: 10

Leu Glu Ser Thr Pro Lys Met Lys
1               5

<210> SEQ ID NO 11
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 11

Ser Val Ser Val Gly Met Lys Pro Ser Pro Arg Pro
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 12

Leu Asp Val Glu Ser Tyr Lys Gly Thr Ser Met Pro
1               5                   10

```
<210> SEQ ID NO 13
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 13

Arg Val Pro Asn Lys Thr Val Thr Val Asp Gly Ala
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 14

Asp Arg His Lys Ser Lys Tyr Ser Ser Thr Lys Ser
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 15

Lys Asn Phe Pro Gln Gln Lys Glu Phe Pro Leu Ser
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 16

Gln Arg Asn Ser Pro Pro Ala Met Ser Arg Arg Asp
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 17

Thr Arg Lys Pro Asn Met Pro His Gly Gln Tyr Leu
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 18

Lys Pro Pro His Leu Ala Lys Leu Pro Phe Thr Thr
1               5                   10

<210> SEQ ID NO 19
```

```
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 19

Asn Lys Arg Pro Pro Thr Ser His Arg Ile His Ala
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 20

Asn Leu Pro Arg Tyr Gln Pro Pro Cys Lys Pro Leu
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 21

Arg Pro Pro Trp Lys Lys Pro Ile Pro Pro Ser Glu
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 22

Arg Gln Arg Pro Lys Asp His Phe Phe Ser Arg Pro
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Hair Binding Peptide Domain
<220> FEATURE:
<221> NAME/KEY: MISC_FEATURE
<222> LOCATION: (6)..(6)
<223> OTHER INFORMATION: X= T or P
<220> FEATURE:
<221> NAME/KEY: MISC_FEATURE
<222> LOCATION: (12)..(12)
<223> OTHER INFORMATION: X= E or A

<400> SEQUENCE: 23

Ser Val Pro Asn Lys Xaa Val Thr Val Asp Gly Xaa
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Hair Binding Peptide Domain
```

```
<400> SEQUENCE: 24

Thr Thr Lys Trp Arg His Arg Ala Pro Val Ser Pro
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 25

Trp Leu Gly Lys Asn Arg Ile Lys Pro Arg Ala Ser
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 26

Ser Asn Phe Lys Thr Pro Leu Pro Leu Thr Gln Ser
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 27

Lys Glu Leu Gln Thr Arg Asn Val Val Gln Arg Glu
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 28

Gly Met Pro Ala Met His Trp Ile His Pro Phe Ala
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 29

Thr Pro Thr Ala Asn Gln Phe Thr Gln Ser Val Pro
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 30
```

```
Ala Ala Gly Leu Ser Gln Lys His Glu Arg Asn Arg
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 31

Glu Thr Val His Gln Thr Pro Leu Ser Asp Arg Pro
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 32

Leu Pro Ala Leu His Ile Gln Arg His Pro Arg Met
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 33

Gln Pro Ser His Ser Gln Ser His Asn Leu Arg Ser
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 34

Arg Gly Ser Gln Lys Ser Lys Pro Pro Arg Pro Pro
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 35

Thr His Thr Gln Lys Thr Pro Leu Leu Tyr Tyr His
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 36
```

```
Thr Lys Gly Ser Ser Gln Ala Ile Leu Lys Ser Thr
1               5                   10
```

```
<210> SEQ ID NO 37
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 37

Asp Leu His Thr Val Tyr His
1               5
```

```
<210> SEQ ID NO 38
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 38

His Ile Lys Pro Pro Thr Arg
1               5
```

```
<210> SEQ ID NO 39
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 39

His Pro Val Trp Pro Ala Ile
1               5
```

```
<210> SEQ ID NO 40
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 40

Met Pro Leu Tyr Tyr Leu Gln
1               5
```

```
<210> SEQ ID NO 41
<211> LENGTH: 26
<212> TYPE: PRT
<213> ORGANISM: Artificial Sequence
<220> FEATURE:
<223> OTHER INFORMATION: Hair Binding Peptide Domain

<400> SEQUENCE: 41

His Leu Thr Val Pro Trp Arg Gly Gly Gly Ser Ala Val Pro Phe Tyr
1               5                   10                  15

Ser His Ser Gln Ile Thr Leu Pro Asn His
            20                  25
```

```
<210> SEQ ID NO 42
<211> LENGTH: 41
<212> TYPE: PRT
<213> ORGANISM: Artificial Sequence
<220> FEATURE:
<223> OTHER INFORMATION: Hair Binding Peptide Domain
```

```
<400> SEQUENCE: 42

Gly Pro His Asp Thr Ser Ser Gly Gly Val Arg Pro Asn Leu His His
1               5                   10                  15

Thr Ser Lys Lys Glu Lys Arg Glu Asn Arg Lys Val Pro Phe Tyr Ser
            20                  25                  30

His Ser Val Thr Ser Arg Gly Asn Val
        35                  40

<210> SEQ ID NO 43
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 43

Lys His Pro Thr Tyr Arg Gln
1               5

<210> SEQ ID NO 44
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 44

His Pro Met Ser Ala Pro Arg
1               5

<210> SEQ ID NO 45
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 45

Met Pro Lys Tyr Tyr Leu Gln
1               5

<210> SEQ ID NO 46
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 46

Met His Ala His Ser Ile Ala
1               5

<210> SEQ ID NO 47
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 47

Thr Ala Ala Thr Thr Ser Pro
1               5

<210> SEQ ID NO 48
<211> LENGTH: 7
```

```
<212> TYPE: PRT
<213> ORGANISM: Artificial Sequence
<220> FEATURE:
<223> OTHER INFORMATION: Hair Binding Peptide Domain

<400> SEQUENCE: 48

Leu Gly Ile Pro Gln Asn Leu
1               5

<210> SEQ ID NO 49
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 49

Ala Lys Pro Ile Ser Gln His Leu Gln Arg Gly Ser
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 50

Ala Pro Pro Thr Pro Ala Ala Ala Ser Ala Thr Thr
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 51

Asp Pro Thr Glu Gly Ala Arg Arg Thr Ile Met Thr
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 52

Glu Gln Ile Ser Gly Ser Leu Val Ala Ala Pro Trp
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 53

Leu Asp Thr Ser Phe Pro Pro Val Pro Phe His Ala
1               5                   10

<210> SEQ ID NO 54
<211> LENGTH: 11
<212> TYPE: PRT
```

```
<213> ORGANISM: Artificial Sequence
<220> FEATURE:
<223> OTHER INFORMATION: Hair Binding Peptide Domain

<400> SEQUENCE: 54

Leu Pro Arg Ile Ala Asn Thr Trp Ser Pro Ser
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 55

Arg Thr Asn Ala Ala Asp His Pro Ala Ala Val Thr
1               5                   10

<210> SEQ ID NO 56
<211> LENGTH: 12
<212> TYPE: PRT
<213> ORGANISM: Artificial Sequence
<220> FEATURE:
<223> OTHER INFORMATION: HairBinding Peptide Domain

<400> SEQUENCE: 56

Ser Leu Asn Trp Val Thr Ile Pro Gly Pro Lys Ile
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 57

Thr Asp Met Gln Ala Pro Thr Lys Ser Tyr Ser Asn
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 58

Thr Ile Met Thr Lys Ser Pro Ser Leu Ser Cys Gly
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 59

Thr Pro Ala Leu Asp Gly Leu Arg Gln Pro Leu Arg
1               5                   10

<210> SEQ ID NO 60
<211> LENGTH: 12
<212> TYPE: PRT
<213> ORGANISM: Artificial Sequence
```

```
<220> FEATURE:
<223> OTHER INFORMATION: Hair Binding Peptide Domain

<400> SEQUENCE: 60

Thr Tyr Pro Ala Ser Arg Leu Pro Leu Leu Ala Pro
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 61

Thr Tyr Pro Ala Ser Arg Leu Pro Leu Leu Ala Pro
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 62

Thr Asp Pro Thr Pro Phe Ser Ile Ser Pro Glu Arg
1               5                   10

<210> SEQ ID NO 63
<211> LENGTH: 20
<212> TYPE: PRT
<213> ORGANISM: Artificial Sequence
<220> FEATURE:
<223> OTHER INFORMATION: Hair Binding Peptide Domain

<400> SEQUENCE: 63

Cys Ala Ala Gly Cys Cys Thr Cys Ala Gly Cys Gly Ala Cys Cys Gly
1               5                   10                  15

Ala Ala Thr Ala
            20

<210> SEQ ID NO 64
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 64

Trp His Asp Lys Pro Gln Asn Ser Ser Lys Ser Thr
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 65

Asn Glu Val Pro Ala Arg Asn Ala Pro Trp Leu Val
1               5                   10

<210> SEQ ID NO 66
<211> LENGTH: 13
```

```
<212> TYPE: PRT
<213> ORGANISM: Artificial Sequence
<220> FEATURE:
<223> OTHER INFORMATION: Hair Binding Peptide Domain

<400> SEQUENCE: 66

Asn Ser Pro Gly Tyr Gln Ala Asp Ser Val Ala Ile Gly
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 67

Thr Gln Asp Ser Ala Gln Lys Ser Pro Ser Pro Leu
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 68

Thr Pro Pro Glu Leu Leu His Gly Asp Pro Arg Ser
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 69

Thr Pro Pro Thr Asn Val Leu Met Leu Ala Thr Lys
1               5                   10

<210> SEQ ID NO 70
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 70

Asn Thr Ser Gln Leu Ser Thr
1               5

<210> SEQ ID NO 71
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 71

Asn Thr Pro Lys Glu Asn Trp
1               5

<210> SEQ ID NO 72
<211> LENGTH: 7
<212> TYPE: PRT
```

```
<213> ORGANISM: Artificial Sequence
<220> FEATURE:
<223> OTHER INFORMATION: Hair Binding Peptide Domain

<400> SEQUENCE: 72

Asn Thr Pro Ala Ser Asn Arg
1               5

<210> SEQ ID NO 73
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 73

Pro Arg Gly Met Leu Ser Thr
1               5

<210> SEQ ID NO 74
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 74

Pro Pro Thr Tyr Leu Ser Thr
1               5

<210> SEQ ID NO 75
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 75

Thr Ile Pro Thr His Arg Gln His Asp Tyr Arg Ser
1               5                   10

<210> SEQ ID NO 76
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 76

Thr Pro Pro Thr His Arg Leu
1               5

<210> SEQ ID NO 77
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 77

Leu Pro Thr Met Ser Thr Pro
1               5

<210> SEQ ID NO 78
<211> LENGTH: 7
<212> TYPE: PRT
<213> ORGANISM: Artificial Sequence
```

```
<220> FEATURE:
<223> OTHER INFORMATION: Hair Binding Peptide Domain

<400> SEQUENCE: 78

Leu Gly Thr Asn Ser Thr Pro
1               5

<210> SEQ ID NO 79
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 79

Thr Pro Leu Thr Gly Ser Thr Asn Leu Leu Ser Ser
1               5                   10

<210> SEQ ID NO 80
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 80

Thr Pro Leu Thr Lys Glu Thr
1               5

<210> SEQ ID NO 81
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 81

Gln Gln Ser His Asn Pro Pro
1               5

<210> SEQ ID NO 82
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 82

Thr Gln Pro His Asn Pro Pro
1               5

<210> SEQ ID NO 83
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 83

Ser Thr Asn Leu Leu Arg Thr Ser Thr Val His Pro
1               5                   10

<210> SEQ ID NO 84
<211> LENGTH: 12
<212> TYPE: PRT
<213> ORGANISM: Artificial Sequence
<220> FEATURE:
```

-continued

<223> OTHER INFORMATION: Hair Binding Peptide Domain

<400> SEQUENCE: 84

His Thr Gln Pro Ser Tyr Ser Ser Thr Asn Leu Phe
1               5                   10

<210> SEQ ID NO 85
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 85

Ser Leu Leu Ser Ser His Ala
1               5

<210> SEQ ID NO 86
<211> LENGTH: 12
<212> TYPE: PRT
<213> ORGANISM: Artificial Sequence
<220> FEATURE:
<223> OTHER INFORMATION: Hair Binding Peptide Domain

<400> SEQUENCE: 86

Gln Gln Ser Ser Ile Ser Leu Ser Ser His Ala Val
1               5                   10

<210> SEQ ID NO 87
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 87

Asn Ala Ser Pro Ser Ser Leu
1               5

<210> SEQ ID NO 88
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 88

His Ser Pro Ser Ser Leu Arg
1               5

<210> SEQ ID NO 89
<211> LENGTH: 7
<212> TYPE: PRT
<213> ORGANISM: Artificial Sequence
<220> FEATURE:
<223> OTHER INFORMATION: Hair Binding Peptide Domain
<220> FEATURE:
<221> NAME/KEY: MISC_FEATURE
<222> LOCATION: (2)..(2)
<223> OTHER INFORMATION: X= H, R or N

<400> SEQUENCE: 89

Lys Xaa Ser His His Thr His
1               5

<210> SEQ ID NO 90
<211> LENGTH: 7

```
<212> TYPE: PRT
<213> ORGANISM: Artificial Sequence
<220> FEATURE:
<223> OTHER INFORMATION: Hair Binding Peptide Domain
<220> FEATURE:
<221> NAME/KEY: MISC_FEATURE
<222> LOCATION: (2)..(2)
<223> OTHER INFORMATION: X=H or Ror N
<220> FEATURE:
<221> NAME/KEY: MISC_FEATURE
<222> LOCATION: (2)..(2)
<223> OTHER INFORMATION: X= H, R, or N

<400> SEQUENCE: 90

Glu Xaa Ser His His Thr His
1               5

<210> SEQ ID NO 91
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 91

Leu Glu Ser Thr Ser Leu Leu
1               5

<210> SEQ ID NO 92
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 92

Thr Pro Leu Thr Lys Glu Thr
1               5

<210> SEQ ID NO 93
<211> LENGTH: 7
<212> TYPE: PRT
<213> ORGANISM: Artificial Sequence
<220> FEATURE:
<223> OTHER INFORMATION: Hair Binding Peptide Domain

<400> SEQUENCE: 93

Lys Gln Ser His Asn Pro Pro
1               5

<210> SEQ ID NO 94
<211> LENGTH: 15
<212> TYPE: PRT
<213> ORGANISM: Artificial Sequence
<220> FEATURE:
<223> OTHER INFORMATION: Hair-binding peptide

<400> SEQUENCE: 94

Ser Thr Leu His Lys Tyr Lys Ser Gln Asp Pro Thr Pro His His
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Hair-binding peptide

<400> SEQUENCE: 95
```

```
His Asp His Lys Asn Gln Lys Glu Thr His Gln Arg His Ala Ala
1               5                   10                  15

<210> SEQ ID NO 96
<211> LENGTH: 20
<212> TYPE: PRT
<213> ORGANISM: Artificial Sequence
<220> FEATURE:
<223> OTHER INFORMATION: Hair-binding peptide

<400> SEQUENCE: 96

His Asn His Met Gln Glu Arg Tyr Thr Asp Pro Gln His Ser Pro Ser
1               5                   10                  15

Val Asn Gly Leu
            20

<210> SEQ ID NO 97
<211> LENGTH: 20
<212> TYPE: PRT
<213> ORGANISM: Artificial Sequence
<220> FEATURE:
<223> OTHER INFORMATION: Hair-binding peptide

<400> SEQUENCE: 97

Thr Ala Glu Ile Asp Ser Ser Lys Asn Pro Asn Pro His Pro Gln Arg
1               5                   10                  15

Ser Trp Thr Asn
            20

<210> SEQ ID NO 98
<211> LENGTH: 7
<212> TYPE: PRT
<213> ORGANISM: Artificial sequence
<220> FEATURE:
<223> OTHER INFORMATION: Skin Binding Peptide Domain

<400> SEQUENCE: 98

Phe Thr Gln Ser Leu Pro Arg
1               5

<210> SEQ ID NO 99
<211> LENGTH: 12
<212> TYPE: PRT
<213> ORGANISM: Artificial Sequence
<220> FEATURE:
<223> OTHER INFORMATION: Skin Binding Peptide Domain

<400> SEQUENCE: 99

Thr Pro Phe His Ser Pro Glu Asn Ala Pro Gly Ser
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Skin Binding Peptide Domain

<400> SEQUENCE: 100

Lys Gln Ala Thr Phe Pro Pro Asn Pro Thr Ala Tyr
1               5                   10

<210> SEQ ID NO 101
<211> LENGTH: 12
<212> TYPE: PRT
```

```
<213> ORGANISM: Artificial Sequence
<220> FEATURE:
<223> OTHER INFORMATION: Skin Binding Peptide Domain

<400> SEQUENCE: 101

His Gly His Met Val Ser Thr Ser Gln Leu Ser Ile
1               5                   10

<210> SEQ ID NO 102
<211> LENGTH: 7
<212> TYPE: PRT
<213> ORGANISM: Artificial Sequence
<220> FEATURE:
<223> OTHER INFORMATION: Skin Binding Peptide Domain

<400> SEQUENCE: 102

Leu Ser Pro Ser Arg Met Lys
1               5

<210> SEQ ID NO 103
<211> LENGTH: 7
<212> TYPE: PRT
<213> ORGANISM: Artificial Sequence
<220> FEATURE:
<223> OTHER INFORMATION: Skin Binding Peptide Domain

<400> SEQUENCE: 103

Leu Pro Ile Pro Arg Met Lys
1               5

<210> SEQ ID NO 104
<211> LENGTH: 7
<212> TYPE: PRT
<213> ORGANISM: Artificial Sequence
<220> FEATURE:
<223> OTHER INFORMATION: Skin Binding Peptide Domain

<400> SEQUENCE: 104

His Gln Arg Pro Tyr Leu Thr
1               5

<210> SEQ ID NO 105
<211> LENGTH: 7
<212> TYPE: PRT
<213> ORGANISM: Artificial Sequence
<220> FEATURE:
<223> OTHER INFORMATION: Skin Binding Peptide Domain

<400> SEQUENCE: 105

Phe Pro Pro Leu Leu Arg Leu
1               5

<210> SEQ ID NO 106
<211> LENGTH: 12
<212> TYPE: PRT
<213> ORGANISM: Artificial Sequence
<220> FEATURE:
<223> OTHER INFORMATION: Nail Binding Peptide Domain

<400> SEQUENCE: 106

Ala Leu Pro Arg Ile Ala Asn Thr Trp Ser Pro Ser
1               5                   10

<210> SEQ ID NO 107
<211> LENGTH: 12
<212> TYPE: PRT
<213> ORGANISM: Artificial Sequence
```

<220> FEATURE:
<223> OTHER INFORMATION: Nail Binding Peptide Domain

<400> SEQUENCE: 107

Tyr Pro Ser Phe Ser Pro Thr Tyr Arg Pro Ala Phe
1               5                   10

<210> SEQ ID NO 108
<211> LENGTH: 17
<212> TYPE: PRT
<213> ORGANISM: Artificial sequence
<220> FEATURE:
<223> OTHER INFORMATION: antimicrobial peptide sequence

<400> SEQUENCE: 108

Pro Lys Gly Leu Lys Lys Leu Leu Lys Gly Leu Lys Lys Leu Leu Lys
1               5                   10                  15

Leu

<210> SEQ ID NO 109
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 109

Lys Gly Leu Lys Lys Leu Leu Lys Gly Leu Lys Lys Leu Leu Lys Leu
1               5                   10                  15

<210> SEQ ID NO 110
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 110

Lys Gly Leu Lys Lys Leu Leu Lys Leu Leu Lys Lys Leu Leu Lys Leu
1               5                   10                  15

<210> SEQ ID NO 111
<211> LENGTH: 14
<212> TYPE: PRT
<213> ORGANISM: Artificial Sequence
<220> FEATURE:
<223> OTHER INFORMATION: Antimicrobial peptide sequence

<400> SEQUENCE: 111

Leu Lys Lys Leu Leu Lys Leu Leu Lys Lys Leu Leu Lys Leu
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Antimicrobial peptide sequence

<400> SEQUENCE: 112

Leu Lys Lys Leu Leu Lys Leu Leu Lys Lys Leu Leu
1               5                   10

<210> SEQ ID NO 113
<211> LENGTH: 17
<212> TYPE: PRT

<213> ORGANISM: Artificial Sequence
<220> FEATURE:
<223> OTHER INFORMATION: Antimicrobial peptide sequences

<400> SEQUENCE: 113

Val Ala Lys Lys Leu Ala Lys Leu Ala Lys Leu Ala Lys Leu Ala
1               5                   10                  15
Leu

<210> SEQ ID NO 114
<211> LENGTH: 13
<212> TYPE: PRT
<213> ORGANISM: Artificial Sequence
<220> FEATURE:
<223> OTHER INFORMATION: Antimicrobial peptide sequences

<400> SEQUENCE: 114

Phe Ala Lys Leu Leu Ala Lys Ala Leu Lys Lys Leu Leu
1               5                   10

<210> SEQ ID NO 115
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 115

Lys Gly Leu Lys Lys Gly Leu Lys Leu Leu Lys Lys Leu Leu Lys Leu
1               5                   10                  15

<210> SEQ ID NO 116
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 116

Lys Gly Leu Lys Lys Leu Leu Lys Leu Gly Lys Lys Leu Leu Lys Leu
1               5                   10                  15

<210> SEQ ID NO 117
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 117

Lys Gly Leu Lys Lys Leu Gly Lys Leu Leu Lys Lys Leu Leu Lys Leu
1               5                   10                  15

<210> SEQ ID NO 118
<211> LENGTH: 16
<212> TYPE: PRT
<213> ORGANISM: Artificial Sequence
<220> FEATURE:
<223> OTHER INFORMATION: Antimicrobial peptide sequence

<400> SEQUENCE: 118

Lys Gly Leu Lys Lys Leu Leu Lys Leu Leu Lys Lys Gly Leu Lys Leu
1               5                   10                  15

<210> SEQ ID NO 119
<211> LENGTH: 16

```
<212> TYPE: PRT
<213> ORGANISM: Artificial Sequence
<220> FEATURE:
<223> OTHER INFORMATION: Antimicrobial peptide sequence

<400> SEQUENCE: 119

Lys Gly Leu Lys Lys Leu Leu Lys Leu Leu Lys Lys Leu Gly Lys Leu
1               5                   10                  15

<210> SEQ ID NO 120
<211> LENGTH: 19
<212> TYPE: PRT
<213> ORGANISM: Artificial Sequence
<220> FEATURE:
<223> OTHER INFORMATION: Antimicrobial peptide sequences

<400> SEQUENCE: 120

Phe Ala Leu Ala Leu Lys Ala Leu Lys Lys Leu Lys Lys Ala Leu Lys
1               5                   10                  15

Lys Ala Leu

<210> SEQ ID NO 121
<211> LENGTH: 17
<212> TYPE: PRT
<213> ORGANISM: Artificial Sequence
<220> FEATURE:
<223> OTHER INFORMATION: Antimicrobial peptide sequence

<400> SEQUENCE: 121

Phe Ala Lys Lys Leu Ala Lys Leu Ala Lys Lys Leu Ala Lys Leu Ala
1               5                   10                  15

Leu

<210> SEQ ID NO 122
<211> LENGTH: 13
<212> TYPE: PRT
<213> ORGANISM: Artificial Sequence
<220> FEATURE:
<223> OTHER INFORMATION: Antimicrobial peptide sequences

<400> SEQUENCE: 122

Phe Ala Lys Leu Leu Ala Lys Leu Ala Lys Lys Leu Leu
1               5                   10

<210> SEQ ID NO 123
<211> LENGTH: 15
<212> TYPE: PRT
<213> ORGANISM: Artificial Sequence
<220> FEATURE:
<223> OTHER INFORMATION: Antimicrobial peptide sequences

<400> SEQUENCE: 123

Phe Ala Lys Lys Leu Ala Lys Leu Ala Leu Lys Leu Ala Lys Leu
1               5                   10                  15

<210> SEQ ID NO 124
<211> LENGTH: 10
<212> TYPE: PRT
<213> ORGANISM: Artificial Sequence
<220> FEATURE:
<223> OTHER INFORMATION: Antimicrobial peptide sequences

<400> SEQUENCE: 124

Phe Ala Lys Lys Leu Ala Lys Lys Leu Leu
1               5                   10
```

```
<210> SEQ ID NO 125
<211> LENGTH: 13
<212> TYPE: PRT
<213> ORGANISM: Artificial Sequence
<220> FEATURE:
<223> OTHER INFORMATION: Antimicrobial peptide sequence

<400> SEQUENCE: 125

Phe Ala Lys Leu Leu Ala Lys Leu Ala Lys Lys Val Leu
1               5                   10

<210> SEQ ID NO 126
<211> LENGTH: 13
<212> TYPE: PRT
<213> ORGANISM: Artificial Sequence
<220> FEATURE:
<223> OTHER INFORMATION: Antimicrobial peptide sequences

<400> SEQUENCE: 126

Lys Tyr Lys Lys Ala Leu Lys Lys Leu Ala Lys Leu Leu
1               5                   10

<210> SEQ ID NO 127
<211> LENGTH: 12
<212> TYPE: PRT
<213> ORGANISM: Artificial Sequence
<220> FEATURE:
<223> OTHER INFORMATION: Antimicrobial peptide sequences

<400> SEQUENCE: 127

Phe Ala Leu Leu Lys Ala Leu Leu Lys Lys Ala Leu
1               5                   10

<210> SEQ ID NO 128
<211> LENGTH: 14
<212> TYPE: PRT
<213> ORGANISM: Artificial Sequence
<220> FEATURE:
<223> OTHER INFORMATION: Antimicrobial peptide sequence

<400> SEQUENCE: 128

Lys Arg Leu Phe Lys Lys Leu Lys Phe Ser Leu Arg Lys Tyr
1               5                   10

<210> SEQ ID NO 129
<211> LENGTH: 14
<212> TYPE: PRT
<213> ORGANISM: Artificial Sequence
<220> FEATURE:
<223> OTHER INFORMATION: Antimicrobial peptide sequence

<400> SEQUENCE: 129

Lys Arg Leu Phe Lys Lys Leu Leu Phe Ser Leu Arg Lys Tyr
1               5                   10

<210> SEQ ID NO 130
<211> LENGTH: 14
<212> TYPE: PRT
<213> ORGANISM: Artificial Sequence
<220> FEATURE:
<223> OTHER INFORMATION: Antimicrobial peptide sequence

<400> SEQUENCE: 130

Leu Leu Leu Phe Leu Leu Lys Lys Arg Lys Lys Arg Lys Tyr
1               5                   10
```

```
<210> SEQ ID NO 131
<211> LENGTH: 36
<212> TYPE: PRT
<213> ORGANISM: Hyalophora cecropia

<400> SEQUENCE: 131

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Trp Gly Gln Ala Thr
            20                  25                  30

Gln Ile Ala Lys
        35

<210> SEQ ID NO 132
<211> LENGTH: 23
<212> TYPE: PRT
<213> ORGANISM: Xenopus sp.

<400> SEQUENCE: 132

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 133
<211> LENGTH: 22
<212> TYPE: PRT
<213> ORGANISM: Xenopus sp.

<400> SEQUENCE: 133

Gly Ile Gly Lys Phe Leu Lys Lys Ala Lys Lys Phe Gly Lys Ala Phe
1               5                   10                  15

Val Lys Ile Leu Lys Lys
            20

<210> SEQ ID NO 134
<211> LENGTH: 12
<212> TYPE: PRT
<213> ORGANISM: Bos taurus

<400> SEQUENCE: 134

Arg Leu Cys Arg Ile Val Val Ile Arg Val Cys Arg
1               5                   10

<210> SEQ ID NO 135
<211> LENGTH: 13
<212> TYPE: PRT
<213> ORGANISM: Bos sp.

<400> SEQUENCE: 135

Ile Leu Pro Trp Lys Trp Pro Trp Trp Pro Trp Arg Arg
1               5                   10

<210> SEQ ID NO 136
<211> LENGTH: 24
<212> TYPE: PRT
<213> ORGANISM: Homo sapiens

<400> SEQUENCE: 136

Asp Ser His Ala Lys Arg His His Gly Tyr Lys Arg Lys Phe His Glu
1               5                   10                  15

Lys His His Ser His Arg Gly Tyr
            20
```

```
<210> SEQ ID NO 137
<211> LENGTH: 7
<212> TYPE: PRT
<213> ORGANISM: Artificial Sequence
<220> FEATURE:
<223> OTHER INFORMATION: Pigment binding peptide sequence

<400> SEQUENCE: 137

Met Pro Pro Pro Leu Met Gln
1               5

<210> SEQ ID NO 138
<211> LENGTH: 7
<212> TYPE: PRT
<213> ORGANISM: Artificial Sequence
<220> FEATURE:
<223> OTHER INFORMATION: Pigment binding peptide sequences

<400> SEQUENCE: 138

Phe His Glu Asn Trp Pro Ser
1               5

<210> SEQ ID NO 139
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 139

Arg Thr Ala Pro Thr Thr Pro Leu Leu Leu Ser Leu
1               5                   10

<210> SEQ ID NO 140
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 140

Trp His Leu Ser Trp Ser Pro Val Pro Leu Pro Thr
1               5                   10

<210> SEQ ID NO 141
<211> LENGTH: 7
<212> TYPE: PRT
<213> ORGANISM: Artificial Sequence
<220> FEATURE:
<223> OTHER INFORMATION: Pigment binding peptide sequence

<400> SEQUENCE: 141

Pro His Ala Arg Leu Val Gly
1               5

<210> SEQ ID NO 142
<211> LENGTH: 7
<212> TYPE: PRT
<213> ORGANISM: Artificial Sequence
<220> FEATURE:
<223> OTHER INFORMATION: Pigment binding peptide sequence

<400> SEQUENCE: 142

Asn Ile Pro Tyr His His Pro
1               5
```

-continued

```
<210> SEQ ID NO 143
<211> LENGTH: 7
<212> TYPE: PRT
<213> ORGANISM: Artificial Sequence
<220> FEATURE:
<223> OTHER INFORMATION: Pigment binding peptide sequences

<400> SEQUENCE: 143

Thr Thr Met Pro Ala Ile Pro
1               5

<210> SEQ ID NO 144
<211> LENGTH: 7
<212> TYPE: PRT
<213> ORGANISM: Artificial Sequence
<220> FEATURE:
<223> OTHER INFORMATION: Pigment binding peptide sequence

<400> SEQUENCE: 144

His Asn Leu Pro Pro Arg Ser
1               5

<210> SEQ ID NO 145
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 145

Ala His Lys Thr Gln Met Gly Val Arg Gln Pro Ala
1               5                   10

<210> SEQ ID NO 146
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 146

Ala Asp Asn Val Gln Met Gly Val Ser His Thr Pro
1               5                   10

<210> SEQ ID NO 147
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 147

Ala His Asn Ala Gln Met Gly Val Ser His Pro Pro
1               5                   10

<210> SEQ ID NO 148
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 148

Ala Asp Tyr Val Gly Met Gly Val Ser His Arg Pro
1               5                   10
```

```
<210> SEQ ID NO 149
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 149

Ser Val Ser Val Gly Met Lys Pro Ser Pro Arg Pro
1               5                   10

<210> SEQ ID NO 150
<211> LENGTH: 7
<212> TYPE: PRT
<213> ORGANISM: Artificial Sequence
<220> FEATURE:
<223> OTHER INFORMATION: Pigment binding peptide sequence

<400> SEQUENCE: 150

Tyr Pro Asn Thr Ala Leu Val
1               5

<210> SEQ ID NO 151
<211> LENGTH: 7
<212> TYPE: PRT
<213> ORGANISM: Artificial Sequence
<220> FEATURE:
<223> OTHER INFORMATION: Pigment binding peptide sequences

<400> SEQUENCE: 151

Val Ala Thr Arg Ile Val Ser
1               5

<210> SEQ ID NO 152
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 152

His Ser Leu Lys Asn Ser Met Leu Thr Val Met Ala
1               5                   10

<210> SEQ ID NO 153
<211> LENGTH: 7
<212> TYPE: PRT
<213> ORGANISM: Artificial Sequence
<220> FEATURE:
<223> OTHER INFORMATION: Pigment binding peptide sequences

<400> SEQUENCE: 153

Asn Tyr Pro Thr Gln Ala Pro
1               5

<210> SEQ ID NO 154
<211> LENGTH: 7
<212> TYPE: PRT
<213> ORGANISM: Artificial Sequence
<220> FEATURE:
<223> OTHER INFORMATION: Pigment binding peptide sequences

<400> SEQUENCE: 154

Lys Cys Cys Tyr Ser Val Gly
1               5

<210> SEQ ID NO 155
```

-continued

```
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 155

Arg His Asp Leu Asn Thr Trp Leu Pro Pro Val Lys
1               5                   10

<210> SEQ ID NO 156
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 156

Glu Ile Ser Leu Pro Ala Lys Leu Pro Ser Ala Ser
1               5                   10

<210> SEQ ID NO 157
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 157

Ser Asp Tyr Val Gly Met Arg Pro Ser Pro Arg His
1               5                   10

<210> SEQ ID NO 158
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 158

Ser Asp Tyr Val Gly Met Arg Leu Ser Pro Ser Gln
1               5                   10

<210> SEQ ID NO 159
<211> LENGTH: 12
<212> TYPE: PRT
<213> ORGANISM: Artificial Sequence
<220> FEATURE:
<223> OTHER INFORMATION: Pigment binding peptide sequences

<400> SEQUENCE: 159

Ser Val Ser Val Gly Ile Gln Pro Ser Pro Arg Pro
1               5                   10

<210> SEQ ID NO 160
<211> LENGTH: 12
<212> TYPE: PRT
<213> ORGANISM: Artificial Sequence
<220> FEATURE:
<223> OTHER INFORMATION: Pigment binding peptide sequence

<400> SEQUENCE: 160

Tyr Val Ser Val Gly Ile Lys Pro Ser Pro Arg Pro
1               5                   10

<210> SEQ ID NO 161
<211> LENGTH: 12
```

```
<212> TYPE: PRT
<213> ORGANISM: Artificial Sequence
<220> FEATURE:
<223> OTHER INFORMATION: Pigment binding peptide sequences

<400> SEQUENCE: 161

Tyr Val Cys Glu Gly Ile His Pro Cys Pro Arg Pro
1               5                   10

<210> SEQ ID NO 162
<211> LENGTH: 7
<212> TYPE: PRT
<213> ORGANISM: Artificial Sequence
<220> FEATURE:
<223> OTHER INFORMATION: Cellulose Binding Peptide

<400> SEQUENCE: 162

Val Pro Arg Val Thr Ser Ile
1               5

<210> SEQ ID NO 163
<211> LENGTH: 7
<212> TYPE: PRT
<213> ORGANISM: Artificial Sequence
<220> FEATURE:
<223> OTHER INFORMATION: Cellulose-Binding Peptide

<400> SEQUENCE: 163

Met Ala Asn His Asn Leu Ser
1               5

<210> SEQ ID NO 164
<211> LENGTH: 7
<212> TYPE: PRT
<213> ORGANISM: Artificial Sequence
<220> FEATURE:
<223> OTHER INFORMATION: Cellulose-Binding Peptide

<400> SEQUENCE: 164

Phe His Glu Asn Trp Pro Ser
1               5

<210> SEQ ID NO 165
<211> LENGTH: 12
<212> TYPE: PRT
<213> ORGANISM: Artificial sequence
<220> FEATURE:
<223> OTHER INFORMATION: Cellulose-Binding Peptide

<400> SEQUENCE: 165

Thr His Lys Thr Ser Thr Gln Arg Leu Leu Ala Ala
1               5                   10

<210> SEQ ID NO 166
<211> LENGTH: 12
<212> TYPE: PRT
<213> ORGANISM: Artificial sequence
<220> FEATURE:
<223> OTHER INFORMATION: Cellulose-Binding Peptide

<400> SEQUENCE: 166

Lys Cys Cys Tyr Val Asn Val Gly Ser Val Phe Ser
1               5                   10

<210> SEQ ID NO 167
<211> LENGTH: 12
<212> TYPE: PRT
```

```
<213> ORGANISM: Artificial sequence
<220> FEATURE:
<223> OTHER INFORMATION: Cellulose-Binding Peptide

<400> SEQUENCE: 167

Ala His Met Gln Phe Arg Thr Ser Leu Thr Pro His
1               5                   10

<210> SEQ ID NO 168
<211> LENGTH: 12
<212> TYPE: PRT
<213> ORGANISM: Artificial sequence
<220> FEATURE:
<223> OTHER INFORMATION: Poly(ethylene terephthalate)-Binding Peptide

<400> SEQUENCE: 168

Gly Thr Ser Asp His Met Ile Met Pro Phe Phe Asn
1               5                   10

<210> SEQ ID NO 169
<211> LENGTH: 12
<212> TYPE: PRT
<213> ORGANISM: Artificial sequence
<220> FEATURE:
<223> OTHER INFORMATION: Polymethylmethacrylate binding peptides

<400> SEQUENCE: 169

Ile Pro Trp Trp Asn Ile Arg Ala Pro Leu Asn Ala
1               5                   10

<210> SEQ ID NO 170
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 170

Thr Ala Val Met Asn Val Val Asn Asn Gln Leu Ser
1               5                   10

<210> SEQ ID NO 171
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 171

Val Pro Trp Trp Ala Pro Ser Lys Leu Ser Met Gln
1               5                   10

<210> SEQ ID NO 172
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 172

Met Val Met Ala Pro His Thr Pro Arg Ala Arg Ser
1               5                   10

<210> SEQ ID NO 173
<211> LENGTH: 12
<212> TYPE: PRT
<213> ORGANISM: Artificial Sequence
```

```
<220> FEATURE:
<223> OTHER INFORMATION: Polymethylmethacrylate-binding peptide

<400> SEQUENCE: 173

Thr Tyr Pro Asn Trp Ala His Leu Leu Ser His Tyr
1               5                   10

<210> SEQ ID NO 174
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 174

Thr Pro Trp Trp Arg Ile Thr
1               5

<210> SEQ ID NO 175
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 175

Asp Leu Thr Leu Pro Phe His
1               5

<210> SEQ ID NO 176
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 176

Gly Thr Ser Ile Pro Ala Met
1               5

<210> SEQ ID NO 177
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 177

His His Lys His Val Val Ala
1               5

<210> SEQ ID NO 178
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 178

His His His Lys His Phe Met
1               5

<210> SEQ ID NO 179
<211> LENGTH: 7
<212> TYPE: PRT
<213> ORGANISM: Artificial Sequence
<220> FEATURE:
```

-continued

<223> OTHER INFORMATION: Polymethylmethacrylate-binding peptide

<400> SEQUENCE: 179

His His His Arg His Gln Gly
1               5

<210> SEQ ID NO 180
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 180

His His Trp His Ala Pro Arg
1               5

<210> SEQ ID NO 181
<211> LENGTH: 7
<212> TYPE: PRT
<213> ORGANISM: Artificial Sequence
<220> FEATURE:
<223> OTHER INFORMATION: Nylon-Binding Peptide

<400> SEQUENCE: 181

Lys Thr Pro Pro Thr Arg Pro
1               5

<210> SEQ ID NO 182
<211> LENGTH: 7
<212> TYPE: PRT
<213> ORGANISM: Artificial Sequence
<220> FEATURE:
<223> OTHER INFORMATION: Nylon-Binding Peptide

<400> SEQUENCE: 182

Val Ile Asn Pro Asn Leu Asp
1               5

<210> SEQ ID NO 183
<211> LENGTH: 7
<212> TYPE: PRT
<213> ORGANISM: Artificial Sequence
<220> FEATURE:
<223> OTHER INFORMATION: Nylon-Binding Peptide

<400> SEQUENCE: 183

Lys Val Trp Ile Val Ser Thr
1               5

<210> SEQ ID NO 184
<211> LENGTH: 7
<212> TYPE: PRT
<213> ORGANISM: Artificial Sequence
<220> FEATURE:
<223> OTHER INFORMATION: Nylon-Binding  Peptide

<400> SEQUENCE: 184

Ala Glu Pro Val Ala Met Leu
1               5

<210> SEQ ID NO 185
<211> LENGTH: 7
<212> TYPE: PRT
<213> ORGANISM: Artificial Sequence
<220> FEATURE:
<223> OTHER INFORMATION: Nylon-Binding Peptide

```
<400> SEQUENCE: 185

Ala Glu Leu Val Ala Met Leu
1               5

<210> SEQ ID NO 186
<211> LENGTH: 7
<212> TYPE: PRT
<213> ORGANISM: Artificial Sequence
<220> FEATURE:
<223> OTHER INFORMATION: Nylon-Binding Peptide

<400> SEQUENCE: 186

His Ser Leu Arg Leu Asp Trp
1               5

<210> SEQ ID NO 187
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 187

Glu Ser Ser Tyr Ser Trp Ser Pro Ala Arg Leu Ser
1               5                   10

<210> SEQ ID NO 188
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 188

Gly Pro Leu Lys Leu Leu His Ala Trp Trp Gln Pro
1               5                   10

<210> SEQ ID NO 189
<211> LENGTH: 7
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 189

Asn Ala Leu Thr Arg Pro Val
1               5

<210> SEQ ID NO 190
<211> LENGTH: 7
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 190

Ser Ala Pro Ser Ser Lys Asn
1               5

<210> SEQ ID NO 191
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide
```

-continued

```
<400> SEQUENCE: 191

Ser Val Ser Val Gly Met Lys Pro Ser Pro Arg Pro
1               5                   10

<210> SEQ ID NO 192
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 192

Ser Tyr Tyr Ser Leu Pro Pro Ile Phe His Ile Pro
1               5                   10

<210> SEQ ID NO 193
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 193

Thr Phe Thr Pro Tyr Ser Ile Thr His Ala Leu Leu
1               5                   10

<210> SEQ ID NO 194
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 194

Thr Met Gly Phe Thr Ala Pro Arg Phe Pro His Tyr
1               5                   10

<210> SEQ ID NO 195
<211> LENGTH: 12
<212> TYPE: PRT
<213> ORGANISM: Artificial Sequence
<220> FEATURE:
<223> OTHER INFORMATION: Poly(tetrafluoroethylene)-Binding Peptide

<400> SEQUENCE: 195

Thr Asn Pro Phe Pro Pro Pro Ser Ser Pro Ala
1               5                   10

<210> SEQ ID NO 196
<211> LENGTH: 27
<212> TYPE: PRT
<213> ORGANISM: artificial sequence
<220> FEATURE:
<223> OTHER INFORMATION: Clay-binding peptide

<400> SEQUENCE: 196

Gly His Gly Ser Pro Ser Asn Ser His His Gly Ser Lys Lys Cys Asp
1               5                   10                  15

Met Gly Asn Ser Arg Ala Lys Cys Lys Arg Leu
            20                  25

<210> SEQ ID NO 197
<211> LENGTH: 27
<212> TYPE: PRT
<213> ORGANISM: artificial sequence
<220> FEATURE:
```

<223> OTHER INFORMATION: Clay-binding peptide

<400> SEQUENCE: 197

Ser Asp Arg His Asn Leu Arg Asn Ser Trp Ser Ile Ser Arg His Cys
1               5                   10                  15

Arg Arg Lys Gln Gly Arg Cys Leu Pro Ala His
            20                  25

<210> SEQ ID NO 198
<211> LENGTH: 27
<212> TYPE: PRT
<213> ORGANISM: artificial sequence
<220> FEATURE:
<223> OTHER INFORMATION: Clay-binding peptide

<400> SEQUENCE: 198

Lys Lys Ser Asn Lys Gly His His Pro Ser Ser Lys Gly Lys Gly Pro
1               5                   10                  15

Pro Trp Ser Glu Trp Asp Lys Lys Asn Gly Pro
            20                  25

<210> SEQ ID NO 199
<211> LENGTH: 27
<212> TYPE: PRT
<213> ORGANISM: artificial sequence
<220> FEATURE:
<223> OTHER INFORMATION: Clay-binding peptide

<400> SEQUENCE: 199

Lys Lys Ser Asn Lys Gly Pro His Pro Ser Ser Lys Gly Lys Gly Pro
1               5                   10                  15

Pro Trp Ser Glu Trp Asp Lys Lys Asn Gly Pro
            20                  25

<210> SEQ ID NO 200
<211> LENGTH: 22
<212> TYPE: PRT
<213> ORGANISM: artificial sequence
<220> FEATURE:
<223> OTHER INFORMATION: Clay-binding peptide

<400> SEQUENCE: 200

Val Gly Arg His His Ser Lys Ala Lys Gln Lys Arg Pro His Gly Gly
1               5                   10                  15

Lys Gly Gln Asn Lys Asn
            20

<210> SEQ ID NO 201
<211> LENGTH: 22
<212> TYPE: PRT
<213> ORGANISM: artificial sequence
<220> FEATURE:
<223> OTHER INFORMATION: Clay-binding peptide

<400> SEQUENCE: 201

Val Gly Arg His His Pro Lys Ala Lys Gln Lys Arg Pro His Gly Gly
1               5                   10                  15

Lys Gly Gln Asn Lys Asn
            20

<210> SEQ ID NO 202
<211> LENGTH: 17
<212> TYPE: PRT
<213> ORGANISM: artificial sequence

```
<220> FEATURE:
<223> OTHER INFORMATION: Clay-binding peptide

<400> SEQUENCE: 202

Gly Arg Arg Pro Arg Ala Arg Gly Arg Ser Arg Arg Gly Ser Thr Lys
1               5                   10                  15

Thr

<210> SEQ ID NO 203
<211> LENGTH: 19
<212> TYPE: PRT
<213> ORGANISM: artificial sequence
<220> FEATURE:
<223> OTHER INFORMATION: Clay-binding peptide

<400> SEQUENCE: 203

Leu Gly Val Ile Arg Asn His Val Val Arg Gly Arg Arg His His Gln
1               5                   10                  15

His Val Arg

<210> SEQ ID NO 204
<211> LENGTH: 27
<212> TYPE: PRT
<213> ORGANISM: artificial sequence
<220> FEATURE:
<223> OTHER INFORMATION: Clay-binding peptide

<400> SEQUENCE: 204

Gln Pro Gly Arg Pro Thr Glu Val His Pro Glu Leu Val Arg Lys Ser
1               5                   10                  15

Ala Tyr Leu Val Asn Pro Ser Glu Asp Ile Arg
            20                  25

<210> SEQ ID NO 205
<211> LENGTH: 27
<212> TYPE: PRT
<213> ORGANISM: artificial sequence
<220> FEATURE:
<223> OTHER INFORMATION: Clay-binding peptide

<400> SEQUENCE: 205

His Arg Ser Glu Lys Pro Lys Asn Val Lys Tyr Lys Arg Gly Tyr Trp
1               5                   10                  15

Glu Arg Gly Asn Gln Lys Lys His Gly Pro Gly
            20                  25

<210> SEQ ID NO 206
<211> LENGTH: 27
<212> TYPE: PRT
<213> ORGANISM: artificial sequence
<220> FEATURE:
<223> OTHER INFORMATION: Clay-binding peptide

<400> SEQUENCE: 206

Gly Ser His Lys Arg Arg Gly Ser Tyr Ala Leu Leu Arg Thr Arg Gly
1               5                   10                  15

Val Gly Arg Gln Ala Glu Leu Glu His Leu Leu
            20                  25

<210> SEQ ID NO 207
<211> LENGTH: 27
<212> TYPE: PRT
<213> ORGANISM: artificial sequence
<220> FEATURE:
```

-continued

```
<223> OTHER INFORMATION: Clay-binding peptide

<400> SEQUENCE: 207

Val Gly Glu Lys Pro Arg Arg Lys Ser Lys Gly Ala Lys Ala Lys Lys
1               5                   10                  15

Ala Arg Thr Lys Glu Glu Lys Leu Pro Lys Asn
            20                  25

<210> SEQ ID NO 208
<211> LENGTH: 27
<212> TYPE: PRT
<213> ORGANISM: artificial sequence
<220> FEATURE:
<223> OTHER INFORMATION: Clay-binding peptide

<400> SEQUENCE: 208

Asn Lys Gly His Lys Gln Ser Gly Ser Pro Arg His Ser Asn Lys Lys
1               5                   10                  15

Glu Lys Lys Thr Gln Gln Lys Arg Gly Gln Pro
            20                  25

<210> SEQ ID NO 209
<211> LENGTH: 27
<212> TYPE: PRT
<213> ORGANISM: artificial sequence
<220> FEATURE:
<223> OTHER INFORMATION: Clay-binding peptide

<400> SEQUENCE: 209

His Trp Gly Ser Gln His Lys Thr Gly Leu Arg Asn His Lys Arg Ser
1               5                   10                  15

Arg Arg Asp Ser Leu Gly Lys Arg Gly Thr Asp
            20                  25

<210> SEQ ID NO 210
<211> LENGTH: 27
<212> TYPE: PRT
<213> ORGANISM: artificial sequence
<220> FEATURE:
<223> OTHER INFORMATION: Clay-binding peptide

<400> SEQUENCE: 210

Lys Gly Trp Gly Ser Ser Ser Gly Pro Pro Gly Leu Thr Gly Lys Ala
1               5                   10                  15

Leu Gly Lys Gly Arg Leu Lys Pro Lys Lys Lys
            20                  25

<210> SEQ ID NO 211
<211> LENGTH: 24
<212> TYPE: PRT
<213> ORGANISM: artificial sequence
<220> FEATURE:
<223> OTHER INFORMATION: Clay-binding peptide

<400> SEQUENCE: 211

Ser Ser Lys Ser Gly Ala Pro Phe Arg Val Pro Ile Cys Phe Thr Ala
1               5                   10                  15

Pro Arg Pro Gln Lys Thr Leu Gly
            20

<210> SEQ ID NO 212
<211> LENGTH: 5
<212> TYPE: PRT
<213> ORGANISM: artificial sequence
```

```
<220> FEATURE:
<223> OTHER INFORMATION: Caspase-3 cleavage sequence
<220> FEATURE:
<221> NAME/KEY: MISC_FEATURE
<222> LOCATION: (5)..(5)
<223> OTHER INFORMATION: Xaa = any naturally occurring amino acid except
      Pro, Glu, Asp, Gln, Lys, and Arg.

<400> SEQUENCE: 212

Asp Met Gln Asp Xaa
1               5

<210> SEQ ID NO 213
<211> LENGTH: 32
<212> TYPE: PRT
<213> ORGANISM: artificial sequence
<220> FEATURE:
<223> OTHER INFORMATION: Synthetic construct.  Possible KSI(C4) acid
      cleavage fragment.

<400> SEQUENCE: 213

Met His Thr Pro Glu His Ile Thr Ala Val Val Gln Arg Phe Val Ala
1               5                   10                  15

Ala Leu Asn Ala Gly Asp Leu Asp Gly Ile Val Ala Leu Phe Ala Asp
            20                  25                  30

<210> SEQ ID NO 214
<211> LENGTH: 24
<212> TYPE: PRT
<213> ORGANISM: artificial sequence
<220> FEATURE:
<223> OTHER INFORMATION: Synthetic construct.  Possible KSI(C4) acid
      cleavage fragment.

<400> SEQUENCE: 214

Met His Thr Pro Glu His Ile Thr Ala Val Val Gln Arg Phe Val Ala
1               5                   10                  15

Ala Leu Asn Ala Gly Asp Leu Asp
            20

<210> SEQ ID NO 215
<211> LENGTH: 22
<212> TYPE: PRT
<213> ORGANISM: artificial sequence
<220> FEATURE:
<223> OTHER INFORMATION: Synthetic construct.  Possible KSI(C4) acid
      cleavage fragment.

<400> SEQUENCE: 215

Met His Thr Pro Glu His Ile Thr Ala Val Val Gln Arg Phe Val Ala
1               5                   10                  15

Ala Leu Asn Ala Gly Asp
            20

<210> SEQ ID NO 216
<211> LENGTH: 11
<212> TYPE: PRT
<213> ORGANISM: artificial sequence
<220> FEATURE:
<223> OTHER INFORMATION: Synthetic construct.  Possible KSI(C4) acid
      cleavage fragment.

<400> SEQUENCE: 216

Leu Asp Gly Ile Val Ala Leu Phe Ala Asp Asp
1               5                   10
```

<210> SEQ ID NO 217
<211> LENGTH: 10
<212> TYPE: PRT
<213> ORGANISM: artificial sequence
<220> FEATURE:
<223> OTHER INFORMATION: Synthetic construct. Possible KSI(C4) acid
      cleavage fragment.

<400> SEQUENCE: 217

Leu Asp Gly Ile Val Ala Leu Phe Ala Asp
1               5                   10

<210> SEQ ID NO 218
<211> LENGTH: 9
<212> TYPE: PRT
<213> ORGANISM: artificial sequence
<220> FEATURE:
<223> OTHER INFORMATION: Synthetic construct. Possible KSI(C4) acid
      cleavage fragment.

<400> SEQUENCE: 218

Gly Ile Val Ala Leu Phe Ala Asp Asp
1               5

<210> SEQ ID NO 219
<211> LENGTH: 8
<212> TYPE: PRT
<213> ORGANISM: artificial sequence
<220> FEATURE:
<223> OTHER INFORMATION: Synthetic construct. Possible KSI(C4) acid
      cleavage fragment.

<400> SEQUENCE: 219

Gly Ile Val Ala Leu Phe Ala Asp
1               5

<210> SEQ ID NO 220
<211> LENGTH: 106
<212> TYPE: PRT
<213> ORGANISM: artificial sequence
<220> FEATURE:
<223> OTHER INFORMATION: Synthetic construct. Possible KSI(C4) acid
      cleavage fragment.

<400> SEQUENCE: 220

Leu Asp Gly Ile Val Ala Leu Phe Ala Asp Asp Ala Thr Val Glu Glu
1               5                   10                  15

Pro Val Gly Ser Glu Pro Arg Ser Gly Thr Ala Ala Cys Arg Glu Phe
            20                  25                  30

Tyr Ala Asn Ser Leu Lys Leu Pro Leu Ala Val Glu Leu Thr Gln Glu
        35                  40                  45

Cys Arg Ala Val Ala Asn Glu Ala Ala Phe Ala Phe Thr Val Ser Phe
    50                  55                  60

Glu Tyr Gln Gly Arg Lys Thr Val Val Ala Pro Cys Asp His Phe Arg
65                  70                  75                  80

Phe Asn Gly Ala Gly Lys Val Val Ser Ile Arg Ala Leu Phe Gly Glu
                85                  90                  95

Lys Asn Ile His Ala Cys Gln Gly Ser Asp
            100                 105

<210> SEQ ID NO 221
<211> LENGTH: 104
<212> TYPE: PRT
<213> ORGANISM: artificial sequence
<220> FEATURE:

```
<223> OTHER INFORMATION: Synthetic construct.  Possible KSI(C4) acid
      cleavage fragment.

<400> SEQUENCE: 221

Gly Ile Val Ala Leu Phe Ala Asp Asp Ala Thr Val Glu Glu Pro Val
1               5                   10                  15

Gly Ser Glu Pro Arg Ser Gly Thr Ala Ala Cys Arg Glu Phe Tyr Ala
            20                  25                  30

Asn Ser Leu Lys Leu Pro Leu Ala Val Glu Leu Thr Gln Glu Cys Arg
        35                  40                  45

Ala Val Ala Asn Glu Ala Ala Phe Ala Phe Thr Val Ser Phe Glu Tyr
50                  55                  60

Gln Gly Arg Lys Thr Val Val Ala Pro Cys Asp His Phe Arg Phe Asn
65                  70                  75                  80

Gly Ala Gly Lys Val Val Ser Ile Arg Ala Leu Phe Gly Glu Lys Asn
                85                  90                  95

Ile His Ala Cys Gln Gly Ser Asp
            100

<210> SEQ ID NO 222
<211> LENGTH: 99
<212> TYPE: PRT
<213> ORGANISM: artificial sequence
<220> FEATURE:
<223> OTHER INFORMATION: Synthetic construct.  Possible KSI(C4) acid
      cleavage fragment.

<400> SEQUENCE: 222

Met His Thr Pro Glu His Ile Thr Ala Val Val Gln Arg Phe Val Ala
1               5                   10                  15

Ala Leu Asn Ala Gly Asp Leu Asp Gly Ile Val Ala Leu Phe Ala Asp
            20                  25                  30

Asp Ala Thr Val Glu Glu Pro Val Gly Ser Glu Pro Arg Ser Gly Thr
        35                  40                  45

Ala Ala Cys Arg Glu Phe Tyr Ala Asn Ser Leu Lys Leu Pro Leu Ala
50                  55                  60

Val Glu Leu Thr Gln Glu Cys Arg Ala Val Ala Asn Glu Ala Ala Phe
65                  70                  75                  80

Ala Phe Thr Val Ser Phe Glu Tyr Gln Gly Arg Lys Thr Val Val Ala
                85                  90                  95

Pro Cys Asp

<210> SEQ ID NO 223
<211> LENGTH: 96
<212> TYPE: PRT
<213> ORGANISM: artificial sequence
<220> FEATURE:
<223> OTHER INFORMATION: Synthetic construct.  Possible KSI(C4) acid
      cleavage fragment.

<400> SEQUENCE: 223

Asp Ala Thr Val Glu Glu Pro Val Gly Ser Glu Pro Arg Ser Gly Thr
1               5                   10                  15

Ala Ala Cys Arg Glu Phe Tyr Ala Asn Ser Leu Lys Leu Pro Leu Ala
            20                  25                  30

Val Glu Leu Thr Gln Glu Cys Arg Ala Val Ala Asn Glu Ala Ala Phe
        35                  40                  45

Ala Phe Thr Val Ser Phe Glu Tyr Gln Gly Arg Lys Thr Val Val Ala
    50                  55                  60
```

Pro Cys Asp His Phe Arg Phe Asn Gly Ala Gly Lys Val Val Ser Ile
65                  70                  75                  80

Arg Ala Leu Phe Gly Glu Lys Asn Ile His Ala Cys Gln Gly Ser Asp
                85                  90                  95

<210> SEQ ID NO 224
<211> LENGTH: 77
<212> TYPE: PRT
<213> ORGANISM: artificial sequence
<220> FEATURE:
<223> OTHER INFORMATION: Synthetic construct. Possible KSI(C4) acid
      cleavage fragment.

<400> SEQUENCE: 224

Leu Asp Gly Ile Val Ala Leu Phe Ala Asp Asp Ala Thr Val Glu Glu
1               5                   10                  15

Pro Val Gly Ser Glu Pro Arg Ser Gly Thr Ala Ala Cys Arg Glu Phe
                20                  25                  30

Tyr Ala Asn Ser Leu Lys Leu Pro Leu Ala Val Glu Leu Thr Gln Glu
            35                  40                  45

Cys Arg Ala Val Ala Asn Glu Ala Ala Phe Ala Phe Thr Val Ser Phe
50                  55                  60

Glu Tyr Gln Gly Arg Lys Thr Val Val Ala Pro Cys Asp
65                  70                  75

<210> SEQ ID NO 225
<211> LENGTH: 75
<212> TYPE: PRT
<213> ORGANISM: artificial sequence
<220> FEATURE:
<223> OTHER INFORMATION: Synthetic construct. Possible KSI(C4) acid
      cleavage fragment.

<400> SEQUENCE: 225

Gly Ile Val Ala Leu Phe Ala Asp Asp Ala Thr Val Glu Glu Pro Val
1               5                   10                  15

Gly Ser Glu Pro Arg Ser Gly Thr Ala Ala Cys Arg Glu Phe Tyr Ala
                20                  25                  30

Asn Ser Leu Lys Leu Pro Leu Ala Val Glu Leu Thr Gln Glu Cys Arg
            35                  40                  45

Ala Val Ala Asn Glu Ala Ala Phe Ala Phe Thr Val Ser Phe Glu Tyr
50                  55                  60

Gln Gly Arg Lys Thr Val Val Ala Pro Cys Asp
65                  70                  75

<210> SEQ ID NO 226
<211> LENGTH: 67
<212> TYPE: PRT
<213> ORGANISM: artificial sequence
<220> FEATURE:
<223> OTHER INFORMATION: Synthetic construct. Possible KSI(C4) acid
      cleavage fragment.

<400> SEQUENCE: 226

Asp Ala Thr Val Glu Glu Pro Val Gly Ser Glu Pro Arg Ser Gly Thr
1               5                   10                  15

Ala Ala Cys Arg Glu Phe Tyr Ala Asn Ser Leu Lys Leu Pro Leu Ala
                20                  25                  30

Val Glu Leu Thr Gln Glu Cys Arg Ala Val Ala Asn Glu Ala Ala Phe
            35                  40                  45

```
Ala Phe Thr Val Ser Phe Glu Tyr Gln Gly Arg Lys Thr Val Val Ala
    50                  55                  60

Pro Cys Asp
65

<210> SEQ ID NO 227
<211> LENGTH: 33
<212> TYPE: PRT
<213> ORGANISM: artificial sequence
<220> FEATURE:
<223> OTHER INFORMATION: Synthetic construct.  Possible KSI(C4) acid
      cleavage fragment.

<400> SEQUENCE: 227

Met His Thr Pro Glu His Ile Thr Ala Val Val Gln Arg Phe Val Ala
1               5                   10                  15

Ala Leu Asn Ala Gly Asp Leu Asp Gly Ile Val Ala Leu Phe Ala Asp
            20                  25                  30

Asp

<210> SEQ ID NO 228
<211> LENGTH: 29
<212> TYPE: PRT
<213> ORGANISM: artificial sequence
<220> FEATURE:
<223> OTHER INFORMATION: Synthetic construct.  Possible KSI(C4) acid
      cleavage fragment.

<400> SEQUENCE: 228

His Phe Arg Phe Asn Gly Ala Gly Lys Val Val Ser Ile Arg Ala Leu
1               5                   10                  15

Phe Gly Glu Lys Asn Ile His Ala Cys Gln Gly Ser Asp
            20                  25

<210> SEQ ID NO 229
<211> LENGTH: 20
<212> TYPE: PRT
<213> ORGANISM: artificial sequence
<220> FEATURE:
<223> OTHER INFORMATION: Tooth-binding peptide

<400> SEQUENCE: 229

Ala His Pro Glu Ser Leu Gly Ile Lys Tyr Ala Leu Asp Gly Asn Ser
1               5                   10                  15

Asp Pro His Ala
            20

<210> SEQ ID NO 230
<211> LENGTH: 20
<212> TYPE: PRT
<213> ORGANISM: artificial sequence
<220> FEATURE:
<223> OTHER INFORMATION: Tooth-binding peptide

<400> SEQUENCE: 230

Ala Ser Val Ser Asn Tyr Pro Pro Ile His His Leu Ala Thr Ser Asn
1               5                   10                  15

Thr Thr Val Asn
            20

<210> SEQ ID NO 231
<211> LENGTH: 14
<212> TYPE: PRT
<213> ORGANISM: artificial sequence
```

```
<220> FEATURE:
<223> OTHER INFORMATION: Tooth-binding peptide

<400> SEQUENCE: 231

Asp Glu Cys Met Glu Pro Leu Asn Ala Ala His Cys Trp Arg
1               5                   10

<210> SEQ ID NO 232
<211> LENGTH: 14
<212> TYPE: PRT
<213> ORGANISM: artificial sequence
<220> FEATURE:
<223> OTHER INFORMATION: Tooth-binding peptide

<400> SEQUENCE: 232

Asp Glu Cys Met His Gly Ser Asp Val Glu Phe Cys Thr Ser
1               5                   10

<210> SEQ ID NO 233
<211> LENGTH: 14
<212> TYPE: PRT
<213> ORGANISM: artificial sequence
<220> FEATURE:
<223> OTHER INFORMATION: Tooth-binding peptide

<400> SEQUENCE: 233

Asp Leu Cys Ser Met Gln Met Met Asn Thr Gly Cys His Tyr
1               5                   10

<210> SEQ ID NO 234
<211> LENGTH: 14
<212> TYPE: PRT
<213> ORGANISM: artificial sequence
<220> FEATURE:
<223> OTHER INFORMATION: Tooth-binding peptide

<400> SEQUENCE: 234

Asp Leu Cys Ser Ser Pro Ser Thr Trp Gly Ser Cys Ile Arg
1               5                   10

<210> SEQ ID NO 235
<211> LENGTH: 20
<212> TYPE: PRT
<213> ORGANISM: artificial sequence
<220> FEATURE:
<223> OTHER INFORMATION: Tooth-binding peptide

<400> SEQUENCE: 235

Asp Pro Asn Glu Ser Asn Tyr Glu Asn Ala Thr Thr Val Ser Gln Pro
1               5                   10                  15

Thr Arg His Leu
            20

<210> SEQ ID NO 236
<211> LENGTH: 20
<212> TYPE: PRT
<213> ORGANISM: artificial sequence
<220> FEATURE:
<223> OTHER INFORMATION: Tooth-binding peptide

<400> SEQUENCE: 236

Glu Pro Thr His Pro Thr Met Arg Ala Gln Met His Gln Ser Leu Arg
1               5                   10                  15

Ser Ser Ser Pro
            20
```

```
<210> SEQ ID NO 237
<211> LENGTH: 20
<212> TYPE: PRT
<213> ORGANISM: artificial sequence
<220> FEATURE:
<223> OTHER INFORMATION: Tooth-binding peptide

<400> SEQUENCE: 237

Gly Asn Thr Asp Thr Thr Pro Pro Asn Ala Val Met Glu Pro Thr Val
1               5                   10                  15

Gln His Lys Trp
            20

<210> SEQ ID NO 238
<211> LENGTH: 15
<212> TYPE: PRT
<213> ORGANISM: artificial sequence
<220> FEATURE:
<223> OTHER INFORMATION: Tooth-binding peptide

<400> SEQUENCE: 238

Asn Gly Pro Asp Met Val Gln Ser Val Gly Lys His Lys Asn Ser
1               5                   10                  15

<210> SEQ ID NO 239
<211> LENGTH: 15
<212> TYPE: PRT
<213> ORGANISM: artificial sequence
<220> FEATURE:
<223> OTHER INFORMATION: Tooth-binding peptide

<400> SEQUENCE: 239

Asn Gly Pro Glu Val Arg Gln Ile Pro Ala Asn Phe Glu Lys Leu
1               5                   10                  15

<210> SEQ ID NO 240
<211> LENGTH: 20
<212> TYPE: PRT
<213> ORGANISM: artificial sequence
<220> FEATURE:
<223> OTHER INFORMATION: Tooth-binding peptide

<400> SEQUENCE: 240

Asn Asn Thr Ser Ala Asp Asn Pro Pro Glu Thr Asp Ser Lys His His
1               5                   10                  15

Leu Ser Met Ser
            20

<210> SEQ ID NO 241
<211> LENGTH: 20
<212> TYPE: PRT
<213> ORGANISM: artificial sequence
<220> FEATURE:
<223> OTHER INFORMATION: Tooth-binding peptide

<400> SEQUENCE: 241

Asn Asn Thr Trp Pro Glu Gly Ala Gly His Thr Met Pro Ser Thr Asn
1               5                   10                  15

Ile Arg Gln Ala
            20

<210> SEQ ID NO 242
<211> LENGTH: 20
<212> TYPE: PRT
<213> ORGANISM: artificial sequence
```

```
<220> FEATURE:
<223> OTHER INFORMATION: Tooth-binding peptide

<400> SEQUENCE: 242

Asn Pro Thr Ala Thr Pro His Met Lys Asp Pro Met His Ser Asn Ala
1               5                   10                  15

His Ser Ser Ala
            20

<210> SEQ ID NO 243
<211> LENGTH: 20
<212> TYPE: PRT
<213> ORGANISM: artificial sequence
<220> FEATURE:
<223> OTHER INFORMATION: Tooth-binding peptide

<400> SEQUENCE: 243

Asn Pro Thr Asp His Ile Pro Ala Asn Ser Thr Asn Ser Arg Val Ser
1               5                   10                  15

Lys Gly Asn Thr
            20

<210> SEQ ID NO 244
<211> LENGTH: 15
<212> TYPE: PRT
<213> ORGANISM: artificial sequence
<220> FEATURE:
<223> OTHER INFORMATION: Tooth-binding peptide

<400> SEQUENCE: 244

Asn Pro Thr Asp Ser Thr His Met Met His Ala Arg Asn His Glu
1               5                   10                  15

<210> SEQ ID NO 245
<211> LENGTH: 14
<212> TYPE: PRT
<213> ORGANISM: artificial sequence
<220> FEATURE:
<223> OTHER INFORMATION: Tooth-binding peptide

<400> SEQUENCE: 245

Gln His Cys Ile Thr Glu Arg Leu His Pro Pro Cys Thr Lys
1               5                   10

<210> SEQ ID NO 246
<211> LENGTH: 14
<212> TYPE: PRT
<213> ORGANISM: artificial sequence
<220> FEATURE:
<223> OTHER INFORMATION: Tooth-binding peptide

<400> SEQUENCE: 246

Thr Pro Cys Ala Pro Ala Ser Phe Asn Pro His Cys Ser Arg
1               5                   10

<210> SEQ ID NO 247
<211> LENGTH: 14
<212> TYPE: PRT
<213> ORGANISM: artificial sequence
<220> FEATURE:
<223> OTHER INFORMATION: Tooth-binding peptide

<400> SEQUENCE: 247

Thr Pro Cys Ala Thr Tyr Pro His Phe Ser Gly Cys Arg Ala
1               5                   10
```

```
<210> SEQ ID NO 248
<211> LENGTH: 20
<212> TYPE: PRT
<213> ORGANISM: artificial sequence
<220> FEATURE:
<223> OTHER INFORMATION: Tooth-binding peptide

<400> SEQUENCE: 248

Trp Cys Thr Asp Phe Cys Thr Arg Ser Thr Pro Thr Ser Thr Ser Arg
1               5                   10                  15

Ser Thr Thr Ser
            20

<210> SEQ ID NO 249
<211> LENGTH: 20
<212> TYPE: PRT
<213> ORGANISM: artificial sequence
<220> FEATURE:
<223> OTHER INFORMATION: Tooth-binding peptide

<400> SEQUENCE: 249

Ala Pro Pro Leu Lys Thr Tyr Met Gln Glu Arg Glu Leu Thr Met Ser
1               5                   10                  15

Gln Asn Lys Asp
            20

<210> SEQ ID NO 250
<211> LENGTH: 20
<212> TYPE: PRT
<213> ORGANISM: artificial sequence
<220> FEATURE:
<223> OTHER INFORMATION: Tooth-binding peptide

<400> SEQUENCE: 250

Glu Pro Pro Thr Arg Thr Arg Val Asn Asn His Thr Val Thr Val Gln
1               5                   10                  15

Ala Gln Gln His
            20

<210> SEQ ID NO 251
<211> LENGTH: 14
<212> TYPE: PRT
<213> ORGANISM: artificial sequence
<220> FEATURE:
<223> OTHER INFORMATION: Tooth-binding peptide

<400> SEQUENCE: 251

Gly Tyr Cys Leu Arg Gly Asp Glu Pro Ala Val Cys Ser Gly
1               5                   10

<210> SEQ ID NO 252
<211> LENGTH: 20
<212> TYPE: PRT
<213> ORGANISM: artificial sequence
<220> FEATURE:
<223> OTHER INFORMATION: Tooth-binding peptide

<400> SEQUENCE: 252

Leu Ser Ser Lys Asp Phe Gly Val Thr Asn Thr Asp Gln Arg Thr Tyr
1               5                   10                  15

Asp Tyr Thr Thr
            20

<210> SEQ ID NO 253
```

```
<211> LENGTH: 14
<212> TYPE: PRT
<213> ORGANISM: artificial sequence
<220> FEATURE:
<223> OTHER INFORMATION: Tooth-binding peptide

<400> SEQUENCE: 253

Asn Phe Cys Glu Thr Gln Leu Asp Leu Ser Val Cys Thr Val
1               5                   10

<210> SEQ ID NO 254
<211> LENGTH: 14
<212> TYPE: PRT
<213> ORGANISM: artificial sequence
<220> FEATURE:
<223> OTHER INFORMATION: Tooth-binding peptide

<400> SEQUENCE: 254

Asn Thr Cys Gln Pro Thr Lys Asn Ala Thr Pro Cys Ser Ala
1               5                   10

<210> SEQ ID NO 255
<211> LENGTH: 20
<212> TYPE: PRT
<213> ORGANISM: artificial sequence
<220> FEATURE:
<223> OTHER INFORMATION: Tooth-binding peptide

<400> SEQUENCE: 255

Pro Ser Glu Pro Glu Arg Arg Asp Arg Asn Ile Ala Ala Asn Ala Gly
1               5                   10                  15

Arg Phe Asn Thr
            20

<210> SEQ ID NO 256
<211> LENGTH: 18
<212> TYPE: PRT
<213> ORGANISM: artificial sequence
<220> FEATURE:
<223> OTHER INFORMATION: Tooth-binding peptide

<400> SEQUENCE: 256

Thr His Asn Met Ser His Phe Pro Pro Ser Gly His Pro Lys Arg Thr
1               5                   10                  15

Ala Thr

<210> SEQ ID NO 257
<211> LENGTH: 14
<212> TYPE: PRT
<213> ORGANISM: artificial sequence
<220> FEATURE:
<223> OTHER INFORMATION: Tooth-binding peptide

<400> SEQUENCE: 257

Thr Thr Cys Pro Thr Met Gly Thr Tyr His Val Cys Trp Leu
1               5                   10

<210> SEQ ID NO 258
<211> LENGTH: 20
<212> TYPE: PRT
<213> ORGANISM: artificial sequence
<220> FEATURE:
<223> OTHER INFORMATION: Tooth-binding peptide

<400> SEQUENCE: 258

Tyr Cys Ala Asp His Thr Pro Asp Pro Ala Asn Pro Asn Lys Ile Cys
```

```
1               5                  10                 15

Gly Tyr Ser His
            20

<210> SEQ ID NO 259
<211> LENGTH: 20
<212> TYPE: PRT
<213> ORGANISM: artificial sequence
<220> FEATURE:
<223> OTHER INFORMATION: Tooth-binding peptide

<400> SEQUENCE: 259

Ala Ala Asn Pro His Thr Glu Trp Asp Arg Asp Ala Phe Gln Leu Ala
1               5                  10                 15

Met Pro Pro Lys
            20

<210> SEQ ID NO 260
<211> LENGTH: 20
<212> TYPE: PRT
<213> ORGANISM: artificial sequence
<220> FEATURE:
<223> OTHER INFORMATION: Tooth-binding peptide

<400> SEQUENCE: 260

Asp Leu His Pro Met Asp Pro Ser Asn Lys Arg Pro Asp Asn Pro Ser
1               5                  10                 15

Asp Leu His Thr
            20

<210> SEQ ID NO 261
<211> LENGTH: 14
<212> TYPE: PRT
<213> ORGANISM: artificial sequence
<220> FEATURE:
<223> OTHER INFORMATION: Tooth-binding peptide

<400> SEQUENCE: 261

Glu Ser Cys Val Ser Asn Ala Leu Met Asn Gln Cys Ile Tyr
1               5                  10

<210> SEQ ID NO 262
<211> LENGTH: 20
<212> TYPE: PRT
<213> ORGANISM: artificial sequence
<220> FEATURE:
<223> OTHER INFORMATION: Tooth-binding peptide

<400> SEQUENCE: 262

His Asn Lys Ala Asp Ser Trp Asp Pro Asp Leu Pro Pro His Ala Gly
1               5                  10                 15

Met Ser Leu Gly
            20

<210> SEQ ID NO 263
<211> LENGTH: 20
<212> TYPE: PRT
<213> ORGANISM: artificial sequence
<220> FEATURE:
<223> OTHER INFORMATION: Tooth-binding peptide

<400> SEQUENCE: 263

Leu Asn Asp Gln Arg Lys Pro Gly Pro Pro Thr Met Pro Thr His Ser
1               5                  10                 15
```

Pro Ala Val Gly
        20

<210> SEQ ID NO 264
<211> LENGTH: 14
<212> TYPE: PRT
<213> ORGANISM: artificial sequence
<220> FEATURE:
<223> OTHER INFORMATION: Tooth-binding peptide

<400> SEQUENCE: 264

Asn Thr Cys Ala Thr Ser Pro Asn Ser Tyr Thr Cys Ser Asn
1               5                   10

<210> SEQ ID NO 265
<211> LENGTH: 14
<212> TYPE: PRT
<213> ORGANISM: artificial sequence
<220> FEATURE:
<223> OTHER INFORMATION: Tooth-binding peptide

<400> SEQUENCE: 265

Ser Asp Cys Thr Ala Gly Leu Val Pro Pro Leu Cys Ala Thr
1               5                   10

<210> SEQ ID NO 266
<211> LENGTH: 20
<212> TYPE: PRT
<213> ORGANISM: artificial sequence
<220> FEATURE:
<223> OTHER INFORMATION: Tooth-binding peptide

<400> SEQUENCE: 266

Thr Ile Glu Ser Ser Gln His Ser Arg Thr His Gln Gln Asn Tyr Gly
1               5                   10                  15

Ser Thr Lys Thr
        20

<210> SEQ ID NO 267
<211> LENGTH: 20
<212> TYPE: PRT
<213> ORGANISM: artificial sequence
<220> FEATURE:
<223> OTHER INFORMATION: Tooth-binding peptide

<400> SEQUENCE: 267

Val Gly Thr Met Lys Gln His Pro Thr Thr Thr Gln Pro Pro Arg Val
1               5                   10                  15

Ser Ala Thr Asn
        20

<210> SEQ ID NO 268
<211> LENGTH: 20
<212> TYPE: PRT
<213> ORGANISM: artificial sequence
<220> FEATURE:
<223> OTHER INFORMATION: Tooth-binding peptide

<400> SEQUENCE: 268

Tyr Ser Glu Thr Pro Asn Asp Gln Lys Pro Asn Pro His Tyr Lys Val
1               5                   10                  15

Ser Gly Thr Lys
        20